US007374764B2

(12) United States Patent
Ni et al.

(10) Patent No.: US 7,374,764 B2
(45) Date of Patent: May 20, 2008

(54) CD33-LIKE PROTEIN

(75) Inventors: Jian Ni, Germantown, MD (US); Reiner L. Gentz, Belo Horizonte-Mg (BR); Craig A. Rosen, Laytonsville, MD (US)

(73) Assignee: Human Genome Sciences, Inc., Rockville, MD (US)

( * ) Notice: Subject to any disclaimer, the term of this patent is extended or adjusted under 35 U.S.C. 154(b) by 738 days.

(21) Appl. No.: 10/413,518

(22) Filed: Apr. 15, 2003

(65) Prior Publication Data

US 2003/0166914 A1   Sep. 4, 2003

Related U.S. Application Data

(62) Division of application No. 08/896,537, filed on Jul. 18, 1997, now Pat. No. 6,590,088.

(60) Provisional application No. 60/022,481, filed on Jul. 19, 1996.

(51) Int. Cl.
*G01N 33/53* (2006.01)
*C07K 1/00* (2006.01)
*C07K 14/00* (2006.01)
*C07K 17/00* (2006.01)
*A61K 39/00* (2006.01)
*A61K 38/00* (2006.01)
*A01N 37/18* (2006.01)

(52) U.S. Cl. ........................ 424/185.1; 435/7.1; 514/2; 530/350

(58) Field of Classification Search ...................... None
See application file for complete search history.

(56) References Cited

U.S. PATENT DOCUMENTS 6,225,446 B1 * 5/2001 Altmann et al. ............ 530/351

FOREIGN PATENT DOCUMENTS

| WO | WO 97/20933 A3 | 6/1997 |
| WO | WO 98/53840 A1 | 12/1998 |
| WO | WO 99/06549 A2 | 2/1999 |
| WO | WO 00/53757- | 9/2000 |
| WO | WO 00/53758- | 9/2000 |
| WO | WO 00/73452- | 12/2000 |

OTHER PUBLICATIONS

Avril, et al., "Siglec-5 (CD170) can mediate inhibitory signaling in the absence of immunoreceptor tyrosine-based inhibitory motif phosphorylation", *The Journal of Biological Chemistry*, vol. 280, pp. 19843-19851, 2005.
Connolly, et al., "Human Siglec-5: tissue distribution, novel isoforms and domain specificities for sialic acid-dependent ligand interactions", *British Journal of Haematology*, vol. 119, pp. 221-238, 2002.

Erickson-Miller, et al., "Characterization of Siglec-5 (CD170) expression and functional activity of anti-Siglec-5 antibodies on human phagocytes", *Experimental Haematology*, vol. 31, pp. 382-388, 2003.
Lock, et al., "Expression of CD33-related siglecs on human mononuclear phagocytes, monocyte-derived dendritic cells and plasmacytoid dendritic cells", *Immunobiology*, vol. 209, pp. 199-207, 2004.
Nguyen, et al., "Loss of Siglec expression on T lymphocytes during human evolution", *PNAS*, vol. 103, pp. 7765-7770, 2006.
Rapoport, et al., "Probing sialic acid binding Ig-like lectins (siglecs) with sulfated oligosaccharides", *Biochemistry* (Moscow), vol. 71, pp. 496-504, 2006.
Virgo, et al., "Identification of the CD33-related Siglec receptor, Siglec-5 (CD170), as a useful marker in both normal myelopoiesis and acute myeloid leukaemias", *British Journal of Haematology*, vol. 123, pp. 420-430, 2003.
Andrews, R.G. et al., "Myeloid-Associated Differentiation Antigens on Stem Cells and Their Progeny Identified by Monoclonal Antibodies," *Blood*, 62(1):124-132 (1983).
Applebaum, F.R. et al., "The Use of Radiolabeled Anti-CD33 Antibody to Augment Marrow Irradiation Prior to Marrow Transplantation for Acute Myelogenous Leukemia," *Transplantation*, 54(5):829-833 (1992).
Bernstein I.D. et al., "Treatment of Acute Myeloid Leukemia Cells In Vitro with a Monoclonal Antibody Recognizing a Myeloid Differentiation Antigen Allows Normal Progenitor Cells to be Expressed," *J. Clin. Invest.*, 79:1153-1159 (1987).
Caron, P.C. et al., "Biological and Immunological Features of Humanized M195 (Anti-CD33) Monoclonal Antibodies," *Cancer Res.*, 52(24):6761-6767 (1992).
Caron, P.C. et al., "Murine and Humanized Constructs of Monoclonal Antibody M195 (Anti-CD33) for the Therapy of Acute Myelogenous Leukemia," *Suppl. to Cancer*, 73(3):1049-1056 (1994).
Caron, P.C. et al., "A Phase 1B Trial of Humanized Monoclonal Antibody M195 (Anti-CD33) in Myeloid Leukemia: Specific Targeting Without Immunogenicity," *Blood*, 83(7):1760-1768 (1994).
Freeman, S.D. et al., "Characterization of CD33 as a New Member of the Sialoadhesin Family of Cellular Interaction Molecules," *Blood*, 85(8):2005-2012 (1995).
Griffin, J.D. et al., "A Monoclonal Antibody Reactive with Normal and Leukemic Human Myeloid Progenitor Cells," *Leukemia Res.*, 8(4):521-534 (1984).
Jurcic, J.G. et al., "Radiolabeled Anti-CD33 Monoclonal Antibody M195 for Myeloid Leukemias," *Cancer Res. (Suppl.)*, 55(23):5908s-5910s (1995).
Matutes, E. et al., "Characterization of Myeloid Leukemias with Monoclonal Antibodies 3C5 and MY9," *Hematological Onco.*, 3(3):179-186 (1985).

(Continued)

*Primary Examiner*—Maher M. Haddad
*Assistant Examiner*—Nora M. Rooney

(57) ABSTRACT

The present invention concerns a novel CD33-like protein. In particular, isolated nucleic acid molecules are provided encoding the CD33-like protein. Recombinant CD33-like polypeptides are also provided as are recombinant vectors and host cells. The invention further provides methods useful during tumor or inflammatory disease diagnosis or prognosis and therapeutic treatments targeting cells expressing CD33-like polypeptides.

11 Claims, 5 Drawing Sheets

OTHER PUBLICATIONS

Pierelli, L. et al., "Further Investigations on the expression of HLA-DR, CD33 and CD13 surface antigens in purified bone marrow and peripheral blood CD34+ haematopoietic progenitor cells," *Brit. J. Haematology*, 84:24-30 (1993).

Robertson, M.J. et al., "Human Bone Marrow Depleted of CD33-Positive Cells Mediated Delayed but Durable Reconstitution of Hematopoiesis: Clinical Trial of MY9 Monoclonal Leukemia," *Blood*, 79(9):2229-2236 (1992).

Silla, L.M.R. et al., "Potentiation of lysis of leukaemia cells by a bispecific antibody to CD33 and CD16 (Fc?RIII) expressed by human natural killer (NK) cells," *Brit. J. of Haematology*, 89:712-718 (1995).

Simmons, D. and Seed, B., "Isolation of a cDNA Encoding CD33, a Differentiation Antigen of Myeloid Progenitor Cells," *J. Immuno.*, 141(8):2797-2800 (1988).

Stiff, P.J. et al., "Anti-CD33 Monoclonal Antibody and Etoposide/Cytosine Arabinoside Combinations for the Ex Vivo Purification of Bone Marrow in Acute Nonlymphocytic Leukemia," *Blood*, 77(2):355-362 (1991).

Genbank Database, Accession No. M23197, Simmons, D. and Seed, B. (1994).

Genbank Database, Accession No. H71235, Hillier et al. (1995).

Genbank Report, Accession No. 2411475, Patel, N. et al. (Nov. 1996).

Genbank Report, Accession No. U71383, Patel, N. et al. (Sep. 1997).

NCBI Entrez Nucleotide Query, GenBank Accession No. AA186082, from Marra, M. et al. (Feb. 1997), with Revision History.

NCBI Entrez Nucleotide Query, GenBank Accession No. AA672534, from Marra, M. et al. (Nov. 1997), with Revision History.

NCBI Entrez Nucleotide Query, GenBank Accession No. AA676802, from Hillier, L. et al. (Dec. 1997), with Revision History.

NCBI Entrez Nucleotide Query, GenBank Accession No. T29458, from Adams, M.D. et al. (1995), with Revision History.

NCBI Entrez Nucleotide Query, GenBank Accession No. R96592, from Hillier, L. et al. (1995), with Revision History.

NCBI Entrez Nucleotide Query, GenBank Accession No. AA162826, from Marra, M. et al. (Feb. 1997), with Revision History.

Cornish, A.L. et al., *Blood*, 92(6): 2123-2132 (The American Society of Hematology) (Sep. 1998).

Skolnick et al., "From genes to protein sructure and function: novel applications of computational approaches in the genomic era," *Tibtech*, 18:34-39 (Jan. 2000).

Simmons et al., "Isolation of a cDNA Encoding CD33, A Differentiation Antigen of Myeloid Progenitor Cells," *J. Immunol.*, 141(8):2797-2800 (Oct. 1988).

Patel et al., "OB-BP1/Siglec-6—A Leptin- and Sialic Acid-Binding Protein of the Immunoglobulin Superfamily," *J. Biol. Chem.*, 274(32):22729-22738 (1999).

* cited by examiner

```
                  10                    30                        50
GGCACGAGCTGGGCTGGGGCCCTGGCGGATGGAGACATGCTGCCCCTGCTGCTGCTGCCC
                                         M   L   P   L   L   L   P
            70                    90                        110
CTGCTGTGGGGGGGTCCCTGCAGGAGAAGCCAGTGTACGAGCTGCAAGTGCAGAAGTCG
 L   L   W   G   G   S   L   Q   E   K   P   V   Y   E   L   Q   V   Q   K   S
                130                   150                       170
GTGACGGTGCAGGAGGGCCTGTGCGTCCTTGTGCCCTGCTCCTTCTCTTACCCCTGGAGA
 V   T   V   Q   E   G   L   C   V   L   V   P   C   S   F   S   Y   P   W   R
            190                   210                       230
TCCTGGTATTCCTCTCCCCCACTCTACGTCTACTGGTTCCGGGACGGGGAGATCCCATAC
 S   W   Y   S   S   P   P   L   Y   V   Y   W   F   R   D   G   E   I   P   Y
            250                   270                       290
TACGCTGAGGTTGTGGCCACAAACAACCCAGACAGAAGAGTGAAGCCAGAGACCCAGGGC
 Y   A   E   V   V   A   T   N   N   P   D   R   R   V   K   P   E   T   Q   G
            310                   330                       350
CGATTCCGCCTCCTTGGGGATGTCCAGAAGAAGAACTGCTCCCTGAGCATCGGAGATGCC
 R   F   R   L   L   G   D   V   Q   K   K   N   C   S   L   S   I   G   D   A
            370                   390                       410
AGAATGGAGGACACGGGAAGCTATTTCTTCCGCGTGGAGAGAGGAAGGGATGTAAAATAT
 R   M   E   D   T   G   S   Y   F   F   R   V   E   R   G   R   D   V   K   Y
            430                   450                       470
AGCTACCAACAGAATAAGCTGAACTTGGAGGTGACAGCCCTGATAGAGAAACCCGACATC
 S   Y   Q   Q   N   K   L   N   L   E   V   T   A   L   I   E   K   P   D   I
            490                   510                       530
CACTTTCTGGAGCCTCTGGAGTCCGGCCGCCCCACAAGGCTGAGCTGCAGCCTTCCAGGA
 H   F   L   E   P   L   E   S   G   R   P   T   R   L   S   C   S   L   P   G
            550                   570                       590
TCCTGTGAAGCGGGACCACCTCTCACATTCTCCTGGACGGGGAATGCCCTCAGCCCCCTG
 S   C   E   A   G   P   P   L   T   F   S   W   T   G   N   A   L   S   P   L
            610                   630                       650
GACCCCGAGACCACCCGCTCCTCAGAGCTCACCCTCACCCCCAGGCCCGAGGACCATGGC
 D   P   E   T   T   R   S   S   E   L   T   L   T   P   R   P   E   D   H   G
            670                   690                       710
ACCAACCTCACCTGTCAGATGAAACGCCAAGGAGCTCAGGTGACCACGGAGAGAACTGTC
 T   N   L   T   C   Q   M   K   R   Q   G   A   Q   V   T   T   E   R   T   V
            730                   750                       770
CAGCTCAATGTCTCCTATGCTCCACAGACCATCACCATCTTCAGGAACGGCATAGCCCTA
 Q   L   N   V   S   Y   A   P   Q   T   I   T   I   F   R   N   G   I   A   L
            790                   810                       830
GAGATCCTGCAAAACACCTCATACCTTCCGGTCCTGGAGGGCCAGGCTCTGCGGCTGCTC
 E   I   L   Q   N   T   S   Y   L   P   V   L   E   G   Q   A   L   R   L   L
```

FIG. 1A

```
                850                   870                   890
TGTGATGCTCCCAGCAACCCCCCTGCACACCTGAGCTGGTTCCAGGGCTCCCCTGCCCTG
 C  D  A  P  S  N  P  P  A  H  L  S  W  F  Q  G  S  P  A  L
                910                   930                   950
AACGCCACCCCCATCTCCAATACCGGGATCTTGGAGCTTCGTCGAGTAAGGTCTGCAGAA
 N  A  T  P  I  S  N  T  G  I  L  E  L  R  R  V  R  S  A  E
                970                   990                  1010
AAAGGAGGCTTCACCTGCCGCGCTCAGCACCCGCTGGGCTTCCTGCAAATTTTTCTGAAT
 K  G  G  F  T  C  R  A  Q  H  P  L  G  F  L  Q  I  F  L  N
               1030                  1050                  1070
CTCTCAGTTTACTCCCTCCCACAGTTGCTGGGCCCCTCCTGCTCCTGGGAGGCTGAGGGT
 L  S  V  Y  S  L  P  Q  L  L  G  P  S  C  S  W  E  A  E  G
               1090                  1110                  1130
CTGCACTGCAGATGCTCCTTTCGAGCCTGGCCGGCCCCCTCCCTGTGCTGGCGGCTTGAG
 L  H  C  R  C  S  F  R  A  W  P  A  P  S  L  C  W  R  L  E
               1150                  1170                  1190
GAGAAGCCGCTGGAGGGGAACAGCAGCCAGGGCTCATTCAAGGTCAACTCCAGCTCACCT
 E  K  P  L  E  G  N  S  S  Q  G  S  F  K  V  N  S  S  P
               1210                  1230                  1250
GGTCCCTGGGCCAACAGCTCCCTGATCCTCCACGGGGGGCTCAATTCCGACCTCAAAGTC
 G  P  W  A  N  S  S  L  I  L  H  G  G  L  N  S  D  L  K  V
               1270                  1290                  1310
AGCTGCAAGGCCTGGAACATCTATGGGTCCCAGAGCGGCTCTGTCCTGCTGCTGCAAGGG
 S  C  K  A  W  N  I  Y  G  S  Q  S  G  S  V  L  L  L  Q  G
               1330                  1350                  1370
AGATCGAACCTCGGGACAGGAGTGGTTCCTGCAGCCCTTGGTGGTGCTGGTGTCATGGCC
 R  S  N  L  G  T  G  V  V  P  A  A  L  G  G  A  G  V  M  A
               1390                  1410                  1430
CTGCTCTGTATCTGTCTGTGCCTCATCTTCTTTTTAATAGTGAAAGCCCGCAGGAAGCAA
 L  L  C  I  C  L  C  L  I  F  F  L  I  V  K  A  R  R  K  Q
               1450                  1470                  1490
GCAGCTGGGAGACCAGAGAAAATGGATGATGAAGACCCCATTATGGGTACCATCACCTCG
 A  A  G  R  P  E  K  M  D  D  E  D  P  I  M  G  T  I  T  S
               1510                  1530                  1550
GGTTCCAGGAAGAAGCCCTGGCCAGACAGCCCCGGAGATCAAGCATCTCCTCCTGGGGAT
 G  S  R  K  K  P  W  P  D  S  P  G  D  Q  A  S  P  P  G  D
               1570                  1590                  1610
GCCCCTCCCTTGGAAGAACAAAAGGAGCTCCATTATGCCTCCCTTAGTTTTTCTGAGATG
 A  P  P  L  E  E  Q  K  E  L  H  Y  A  S  L  S  F  S  E  M
               1630                  1650                  1670
AAGTCGAGGGAGCCTAAGGACCAGGAGGCCCCAAGCACCACGGAGTACTCGGAGATCAAG
 K  S  R  E  P  K  D  Q  E  A  P  S  T  T  E  Y  S  E  I  K
```

FIG. 1B

```
              1690                1710               1730
ACAAGCAAGTGAGGATTTGCCCAGAGTTCAGTCCTGGCTGGAGGAGCCACAGCCTGTCTG
 T   S   K   *
              1750                1770               1790
GGGGAAAGGACAAGTCAGGGACCACTTGCTGAAGCACGAAGAGCCCTTGTGGCAATGTTA
              1810                1830               1850
ACATTAACTGATGTTTAAGTGCTCCAAGCAGAGCAGAAAGAAAACAGATGATGGAATTAG
              1870                1890               1910
AGAGGTGGGCTCAAATCTAGGCCCTGGCACTGTCATCAAGCAATTCACTGCATCCCTCTG
              1930                1950               1970
TGCCTCAGTTTCCCATTCTGTAAATCAGAGATCATGCATGCTACCTCAAAGGTTGTTGTG
              1990                2010
AACATTAAAGAAATCAACACATGGAAATCAAAAAAAAAAAAAAAAAAA
```

FIG. 1C

```
  1 MLPLLLLPLLWGGSLQEKPVYELQVQKSVTVQEGLCVLVPCSFSYPWRSW   50
    | |||||||||:|.|.  .| : ||||.||||||||||||||.| .| . :
  1 mplllllpllwagalamdpnfwlqvqesvtvqeglcvlvpctffhpipyy   50

51 YSSPPLYVYWFRDGEIPYYAEVVATNNPDRRVKPETQGRFRLLGDVQKKN  100
    ...|:..||||:|.|    ...||||. |. |..||||||||||. :.|
 51 dknspvhgywfregaiisgdspvatnkldqevqeetqgrfrllgdpsrnn  100

101 CSLSIGDARMEDTGSYFFRVERGRDVKYSYQQNKLNLEVTALIEKPDIHF  150
    ||||.|||. |.||||||:|||  ..||||.  .|.::||.|..:|.| :
101 cslsivdarrrdngsyffrmerg.stkysykspqlsvhvtdlthrpkili  149

151 LEPLESGRPTRLSCSLPGSCEAGPPLTFSWTGNALSPLDPETTRSSELTL  200
    :.||.|:...|.||:. .||.|.| .|||  :.|  ..|:| ||:|| |.:
150 pgtlepghskn1tcsvswaceqgtppifswlsaaptslgprtthssvlii  199

201 TPRPEDHGTNLTCQMKRQGAQVTTERTVQLNVSYAPQTITIFRNGIALEI  250
    ||||:||||||||:| .||.||||||:||||.|.||. |
200 tprpqdhgtnltcqvkfagagvttertiqlnvtyvpqnpt..........  239

251 LQNTSYLPVLEGQALRLLCDAPSNPPAHLSWFQGSPALNATPISNTGILE  300
                                                 |||:
240 .........................................tgif.    243

351 CRCSFRAWPAPSLCWRLEEKPLEGNSSQGSFKVNSSSPGPWANSSLILHG  400
                                .::||
244 ........................pgdgs....................  248

401 GLNSDLKVSCKAWNIYGSQSGSBLLLQGRSNLGTGVVPAALGGAGVMALL  450
                            |: :  .|:|..:|:||||| |||
249 ........................gkqetraglvhgaiggagvtall    271

451 CICLCLIFFLIVKARRKQAAGRPEKMDDEDPIMGTITSGSRKKPWPDSPG  500
    .:|||||| |||.:|:.||  :   :|..|. |. .. .|... .:|.
272 alclcliff.ivkthrrkaartavgsndthpttgsaspkhqknsklhgpt  320

501 DQASPPGDAPPLEEQKELHYASLSFSEMKSREPKDQEAPSTTEYSEIKTS  550
    : .|..|.||..:| :.|||||||.| :|       :... ...||||::|
321 etsscsgaaptvemdeelhyaslnfhgm......npskdtsteysevrtq  364
```

FIG.2

CD33-LIKE PROTEIN

CROSS-REFERENCE TO RELATED APPLICATIONS

This application is a divisional of U.S. application Ser. No. 08/896,537, filed on Jul. 18, 1997, now U.S. Pat. No. 6,590,088, which claims the benefit of the filing date of provisional application 60/022,481 filed on Jul. 19, 1996, each of which is herein incorporated by reference.

BACKGROUND OF THE INVENTION

1. Field of the Invention

The present invention relates to a novel CD33-like protein. In particular, isolated nucleic acid molecules are provided encoding the CD33-like protein. Recombinant CD33-like polypeptides are also provided as are recombinant vectors and host cells. The invention further provides methods useful during tumor or inflammatory disease diagnosis or prognosis and therapeutic treatments targeting cells expressing CD33-like polypeptides.

2. Background Information

CD33 was originally defined on human myeloid cells by a panel of monoclonal antibodies (MoAbs) that recognize a glycoprotein of 67 kD that is restricted in its expression to cells of the hematopoietic system (Peiper S. C. et al., in Knapp W, Dorken B, Gilks W R, Rieber E P, Schmidt R E, Stein H, von dem Borne A E G (eds): *Leucocyte Typing IV. White Cell Differentiation Antigens*. Oxford, UK, Oxford University 1989, p 814; Pierelli L. et al., *Br J Haematol* 84:24 (1993); Andrews R. G. et al., *Blood* 62:124, (1983); Griffin J. D., et al., *Leuk Res* 8:521 (1984)). CD33 is absent from hematopoietic stem cells but is first detected on a subpopulation of mixed colony-forming cells (Pierelli L. et al., *Br J Haematol* 84:24 (1993); Griffin J. D. et al., *Leuk Res* 8:521 (1984)). Expression then continues along the myelomonocytic pathway until it is downregulated on granulocytes but retained by monocytes and tissue macrophages. (Pierelli L. et al., *Br J Haematol* 84:24 (1993); Bernstein I. D. et al., *J Clin Invest* 79:1153 (1987)). The expression pattern of CD33 within the hematopoietic system indicates a potential role in the regulation of myeloid cell differentiation. However, despite its initial identification over 10 years ago (Andrews R. G. et al., *Blood* 62:124 (1983)), the functions and binding properties of CD33 have remained obscure.

CD33 MoAbs are of great importance in the immunodiagnosis of acute leukemias, allowing distinction between myeloid leukemic cells (acute myeloid leukemia (AML) French-American-British classification Ml-7) and the usually CD33-negative cells of lymphoid origin. (Griffin J. D. et al., *Leuk Res* 8:521 (1984); Matutes E. et al., *Haematol Oncol* 3:179 (1985); Bain B. J.: Immunological cytogenetics and other markers, in Bain B J (ed): *Leukaemia Diagnosis: A Guide to FAB Classification*. London, UK, Gower Medical, 1990, p 61). This is especially valuable for the more immature forms of AML, where morphologic criteria are insufficient yet correct categorization is essential for prognostic predictions and the choice of therapy. CD33 MoAbs have also been used in preliminary therapeutic trials, principally for purging of the bone marrow of AML patients, either before transplantation or in case of diseases that are resistant to chemotherapy. (Robertson M. J. et al., *Blood* 79:2229 (1992); Applebaum F. R. et al., *Transplantation* 54:829 (1992); Caron P. C. et al., *Cancer* 73:1049 (1994)). Thus, due to the importance of CD33, there is a clear need to identify and isolate nucleic acid molecules encoding additional polypeptides having CD33-like protein activity.

SUMMARY OF THE INVENTION

The present invention provides isolated nucleic acid molecules comprising a nucleic acid sequence encoding a CD33-like protein whose amino acid sequence is shown in FIG. 1A-1C (SEQ ID NO:2) or a fragment of the polypeptide. The CD33-like protein gene contains an open reading frame encoding a protein of about 551 amino acid residues whose initiation codon is at position 37-39 of the nucleotide sequence shown in FIG. 1A-1C (SEQ ID NO:1), with a leader sequence of about 15 amino acid residues, and a deduced molecular weight of about 60 kDa. The amino acid sequence of the mature CD33-like protein is shown in FIG. 1A-1C (amino acid residues from about 1 to about 536 in SEQ ID NO:2).

Thus, one aspect of the invention provides an isolated nucleic acid molecule comprising a polynucleotide having a nucleotide sequence selected from the group consisting of: (a) a nucleotide sequence encoding the CD33-like protein having the complete amino acid sequence in SEQ ID NO:2; (b) a nucleotide sequence encoding the CD33-like protein having the complete amino acid sequence in SEQ ID NO:2 but minus the N-terminal methionine residue; (c) a nucleotide sequence encoding the mature CD33-like protein having the amino acid sequence at positions from about 1 to about 536 in SEQ ID NO:2; (d) a nucleotide sequence encoding the CD33-like protein having the complete amino acid sequence encoded by the cDNA clone contained in ATCC Deposit No. 97521; (e) a nucleotide sequence encoding the mature CD33-like protein having the amino acid sequence encoded by the cDNA clone contained in ATCC Deposit No. 97521; (f) a nucleotide sequence encoding the CD33-like protein extracellular domain; (g) a nucleotide sequence encoding the CD33-like protein transmembrane domain; (h) a nucleotide sequence encoding the CD33-like protein intracellular domain; (i) a nucleotide sequence encoding the CD33-like protein intracellular and extracellular domains with all or part of the transmembrane domain deleted; and (j) a nucleotide sequence complementary to any of the nucleotide sequences in (a), (b), (c), (d), (e), (f), (g), (h), or (i) above.

Further embodiments of the invention include isolated nucleic acid molecules that comprise a polynucleotide having a nucleotide sequence at least 95% identical, and more preferably at least 96%, 97%, 98% or 99% identical, to any of the nucleotide sequences in (a), (b), (c), (d), (e), (f), (g), (h), (i), or (j) above, or a polynucleotide which hybridizes under stringent hybridization conditions to a polynucleotide in (a), (b), (c), (d), (e), (f), (g), (h), (i), or (j) above. This polynucleotide which hybridizes does not hybridize under stringent hybridization conditions to a polynucleotide having a nucleotide sequence consisting of only A residues or of only T residues. An additional nucleic acid embodiment of the invention relates to an isolated nucleic acid molecule comprising a polynucleotide which encodes the amino acid sequence of an epitope-bearing portion of a CD33-like protein having an amino acid sequence in (a), (b), (c), (d), (e), (f), (g), (h), or (i) above.

The present invention also relates to vectors which include the isolated DNA molecules of the present invention, host cells which are genetically engineered with the recombinant vectors, and the production of CD33-like polypeptides or fragments thereof by recombinant techniques.

The polypeptides of the present invention include the polypeptide encoded by the deposited cDNA, the polypeptide of SEQ ID NO:2 (in particular the mature polypeptide), as well as polypeptides having an amino acid sequence at least 95% identical, more preferably, at least 96% or 99% identical, to the amino acid sequence of the polypeptide encoded by the deposited cDNA or the polypeptide of SEQ ID NO:2.

The invention further provides an isolated CD33-like protein having an amino acid sequence selected from the group consisting of: (a) the amino acid sequence of the CD33-like protein having the complete 551 amino acid sequence, including the leader sequence shown in SEQ ID NO:2; (b) the amino acid sequence of the CD33-like protein having the complete 551 amino acid sequence, including the leader sequence shown in SEQ ID NO:2 but minus the N-terminal methionine residue; (c) the amino acid sequence of the mature CD33-like protein (without the leader) having the amino acid sequence at positions from about 1 to about 536 in SEQ ID NO:2; (d) the amino acid sequence of the CD33-like protein having the complete amino acid sequence, including the leader, encoded by the cDNA clone contained in ATCC Deposit No. 97521;(e) the amino acid sequence of the mature CD33-like protein having the amino acid sequence encoded by the cDNA clone contained in ATCC Deposit No. 97521; (f) the amino acid sequence of the CD33-like protein extracellular domain; (g) the amino acid sequence of the CD33-like protein transmembrane domain; (h) the amino acid sequence of the CD33-like protein intracellular domain; and (i) the amino acid sequence of the CD33-like protein intracellular and extracellular domains with all or part of the transmembrane domain deleted.

An additional embodiment of this aspect of the invention relates to a peptide or polypeptide which has the amino acid sequence of an epitope-bearing portion of a CD33-like polypeptide having an amino acid sequence described in (a), (b), (c), (d), (e), (f), (g), (h), or (i) above. Peptides or polypeptides having the amino acid sequence of an epitope-bearing portion of a CD33-like polypeptide of the invention include portions of such polypeptides with at least six or seven, preferably at least nine, and more preferably at least about 30 amino acids to about 50 amino acids, although epitope-bearing polypeptides of any length up to and including the entire amino acid sequence of a polypeptide of the invention described above also are included in the invention. In another embodiment, the invention provides an isolated antibody that binds specifically to a CD33-like polypeptide having an amino acid sequence described in (a), (b), (c), (d), (e), (f), (g), (h), or (i) above. Such antibodies are useful diagnostically or therapeutically as described below.

The invention further provides a method useful during tumor or inflammatory disease diagnosis, which involves assaying the expression level of the gene encoding the CD33-like protein or the gene copy number in mammalian cells or body fluid and comparing the gene expression level or gene copy number with a standard CD33-like protein gene expression level or gene copy number, whereby an increase in the gene expression level or gene copy number over the standard is indicative of certain tumors or inflammatory disease. By the invention, the above-described method is further useful as a prognostic indicator.

In another embodiment, an in vitro method is provided for purging leukemic hematopoietic cells from the autografts of patients with leukemia. The method involves removing CD33-like antigen-containing hematopoietic cells from bone marrow obtained from the patient with an anti-CD33-like protein monoclonal antibody (MoAb) and complement.

In a further embodiment, the invention provides an in vivo method for selectively killing or inhibiting growth of tumor cells expressing the CD33-like antigen of the present invention, which involves administering to a patient an effective amount of an antagonist to inhibit the CD33-like protein receptor signaling pathway. By the invention, administering such antagonists of the CD33-like protein to a patient is also useful for treating inflammatory disease.

In a still further embodiment, immunotoxins specific for cells expressing the CD33-like protein are provided for selective killing of tumor cells. The immunotoxins of the present invention are further useful according to the method described above for purging leukemic hematopoietic $CD33^+$ cells in vitro.

BRIEF DESCRIPTION OF THE FIGURES

FIG. 1A-1C shows the nucleotide (SEQ ID NO:1) and deduced amino acid (SEQ ID NO:2) sequences of the CD33-like protein. Amino acids from about 1 to about 15 represent the signal peptide (first underlined sequence), amino acids from about 16 to about 422 the extracellular domain (sequence between the first and second underlined sequences) (amino acids from about 1 to about 407 in SEQ ID NO:2), amino acids from about 423 to about 464 the transmembrane domain (second underlined sequence) (amino acids from about 408 to about 449 in SEQ ID NO:2), and amino acids from about 465 to about 551 the intracellular domain (the remaining sequence) (amino acids from about 450 to about 536 in SEQ ID NO:2).

FIG. 2 is an amino acid sequence comparison showing the regions of similarity between the amino acid sequences of the CD33-like protein of the present invention (SEQ ID NO:2) and the human differentiation antigen CD33 (SEQ ID NO:3).

DETAILED DESCRIPTION

Figure 3:
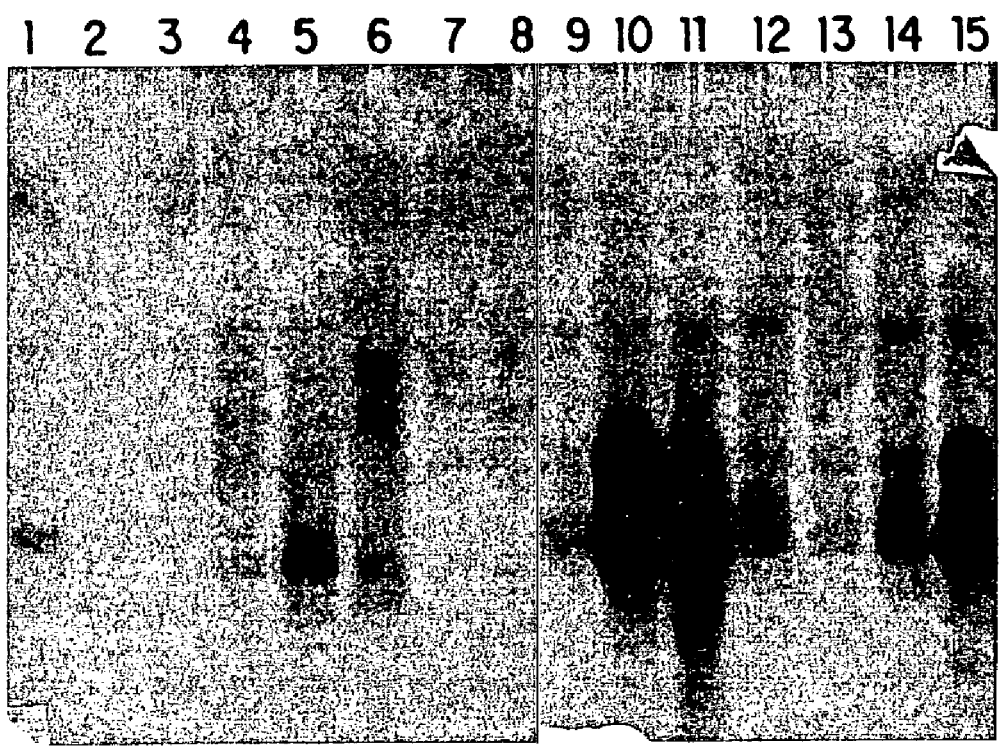
FIG. 3 is a Northern blot showing the tissue distribution of human CD33-like protein mRNA expression. Expression was measured in the following tissues: pancreas (lane 1), kidney (lane 2), skeletal muscle (lane 3), liver (lane 4), lung (lane 5), placenta (lane 6), brain (lane 7), heart (lane 8), fetal liver (lane 9), bone marrow (lane 10), peripheral blood leucocytes (lane 11), appendix (lane 12), thymus (lane 13), lymph node (lane 14), and spleen (lane 15).

The present invention provides isolated nucleic acid molecules comprising a polynucleotide encoding a CD33-like protein having an amino acid sequence shown in FIG. 1A-1C (SEQ ID NO:2), which was determined by sequencing a cloned cDNA. The CD33-like protein of the present invention shares sequence homology with the human differentiation antigen (CD33) (FIG. 2 (SEQ ID NO:3)). The nucleotide sequence shown in FIG. 1A-1C (SEQ ID NO:1) was obtained by sequencing the HMQCD14 clone, which was deposited on Apr. 25, 1996 at the American Type Culture Collection, 10801 University Blvd., Manassas, Va. 20110-2209, USA, and given accession number 97521.

Nucleic Acid Molecules

Unless otherwise indicated, all nucleotide sequences determined by sequencing a DNA molecule herein were determined using an automated DNA sequencer (such as the Model 373 from Applied Biosystems, Inc.), and all amino acid sequences of polypeptides encoded by DNA molecules determined herein were predicted by translation of a DNA sequence determined as above. Therefore, as is known in the art for any DNA sequence determined by this automated approach, any nucleotide sequence determined herein may contain some errors. Nucleotide sequences determined by automation are typically at least about 90% identical, more typically at least about 95% to at least about 99.9% identical to the actual nucleotide sequence of the sequenced DNA molecule. The actual sequence can be more precisely determined by other approaches including manual DNA sequencing methods well known in the art. As is also known in the art, a single insertion or deletion in a determined nucleotide sequence compared to the actual sequence will cause a frame shift in translation of the nucleotide sequence such that the predicted amino acid sequence encoded by a determined nucleotide sequence will be completely different from the amino acid sequence actually encoded by the sequenced DNA molecule, beginning at the point of such an insertion or deletion.

Unless otherwise indicated, each "nucleotide sequence" set forth herein is presented as a sequence of deoxyribonucleotides (abbreviated A, G, C and T). However, by "nucleotide sequence" of a nucleic acid molecule or polynucleotide is intended, for a DNA molecule or polynucleotide, a sequence of deoxyribonucleotides, and for an RNA molecule or polynucleotide, the corresponding sequence of ribonucleotides (A, G, C and U) where each thymidine deoxynucleotide (T) in the specified deoxynucleotide sequence is replaced by the ribonucleotide uridine (U). For instance, reference to an RNA molecule having the sequence of SEQ ID NO:1 set forth using deoxyribonucleotide abbreviations is intended to indicate an RNA molecule having a sequence in which each deoxynucleotide A, G, or C of SEQ ID NO:1 has been replaced by the corresponding ribonucleotide A, G, or C, and each deoxynucleotide T has been replaced by a ribonucleotide U.

Thus, in one aspect, isolated nucleic acid molecules are provided which encode the CD33-like protein. By "isolated" nucleic acid molecule(s) is intended a nucleic acid molecule, DNA or RNA, which has been removed from its native environment. For example, recombinant DNA molecules contained in a vector are considered isolated for the purposes of the present invention. Further examples of isolated DNA molecules include recombinant DNA molecules maintained in heterologous host cells or purified (partially or substantially) DNA molecules in solution. Isolated RNA molecules include in vitro RNA transcripts of the DNA molecules of the present invention. Isolated nucleic acid molecules according to the present invention further include such molecules produced synthetically.

Using the information provided herein, such as the nucleotide sequence set out in FIG. 1A-1C (SEQ ID NO:1), a nucleic acid molecule of the present invention encoding a CD33-like protein may be obtained using standard cloning and screening procedures, such as those for cloning cDNAs using mRNA as starting material. Illustrative of the invention, the nucleic acid molecule described in FIG. 1A-1C (SEQ ID NO:1) was discovered in a cDNA library derived from human activated monocytes. Further, the gene was also found in cDNA libraries derived from the following types of human cells: human eosinophils, spleen, chronic lymphocytic leukemia, human activated neutrophils, and human tonsils.

The CD33-like protein gene contains an open reading frame encoding a full-length protein of about 551 amino acid residues whose initiation codon is at position 37-39 of the nucleotide sequence shown in FIG. 1A-1C (SEQ ID NO:1), and a predicted leader sequence of about 15 amino acid residues, and a deduced molecular weight of about 60 kDa. The amino acid sequence of the predicted mature CD33-like protein is shown in FIG. 1A-1C from amino acid residue 16 to residue 551 (amino acids from about 1 to about 536 in SEQ ID NO:2). The mature CD33-like protein has three main structural domains. These include the extracellular domain, which includes the ligand binding domain, and is predicted to correspond to amino acid residues from about 16 to about 422 in FIG. 1A-1C (amino acids from about 1 to about 407 in SEQ ID NO:2). The mature extracellular domain is predicted to be, about 407 amino acids in length with a molecular weight of about 45 kDa. Another domain is the transmembrane domain, which has been predicted to correspond to about residues 423 to about 464 in FIG. 1A-1C (amino acids from about 408 to about 449 in SEQ ID NO:2). Another domain is the intracellular domain, which has been predicted to correspond to amino acid residue 465 to about 551 in FIG. 1A-1C (amino acids from about 450 to about 536 in SEQ ID NO:2). The CD33-like protein shown in FIG. 1A-1C (SEQ ID NO:2) is about 53% identical and about 64% similar to the human differentiation antigen CD33, which can be accessed on GenBank as Accession No. M23197. As one of ordinary skill would appreciate, due to the possibilities of sequencing errors discussed above, as well as the variability of cleavage sites for leaders in different known proteins, the actual full-length CD33-like protein (including the leader) encoded by the deposited cDNA comprises about 551 amino acids, but may be anywhere in the range of about 545-560 amino acids; and the actual leader sequence of this protein is about 15 amino acids, but may be anywhere in the range of about 12 to about 18 amino acids. It will also be appreciated that reasonable persons of skill in the art may disagree, depending on the criteria used, concerning the exact 'address' of the above described CD33-like protein domains. Thus, for example, the exact location of the CD33-like protein extracellular, intracellular and transmembrane domains in FIG. 1A-1C (SEQ ID NO:2) may vary slightly (e.g., the exact 'address' may differ by about 1 to about 5 residues compared to that shown in FIG. 1A-1C (SEQ ID NO:2)) depending on the criteria used to define the domain.

The present invention also provides the mature form(s) of the CD33-like protein of the present invention. According to the signal hypothesis, proteins secreted by mammalian cells have a signal or secretory leader sequence which is cleaved from the mature protein once export of the growing protein chain across the rough endoplasmic reticulum has been initiated. Most mammalian cells and even insect cells cleave secreted proteins with the same specificity. However, in some cases, cleavage of a secreted protein is not entirely uniform, which results in two or more mature species on the protein. Further, it has long been known that the cleavage specificity of a secreted protein is ultimately determined by the primary structure of the complete protein, that is, it is inherent in the amino acid sequence of the polypeptide. Therefore, the present invention provides a nucleotide sequence encoding the mature CD33-like proteins having the amino acid sequence encoded by the cDNA clone contained in the host identified as ATCC Deposit No. 97521 and as shown in SEQ ID NO:2. By the mature CD33-like protein having the amino acid sequence encoded by the cDNA clone contained in the host identified as ATCC Deposit 97521 is meant the mature form(s) of the CD33-like protein produced by expression in a mammalian cell (e.g., COS cells, as described below) of the complete open reading frame encoded by the human DNA sequence of the clone contained in the vector in the deposited host. As indicated below, the mature CD33-like protein having the amino acid sequence encoded by the cDNA clone contained in ATCC Deposit No. 97521 may or may not differ from the predicted "mature" CD33-like protein shown in SEQ ID NO:2 (amino acids from about 1 to about 536) depending on the accuracy of the predicted cleavage site based on computer analysis.

Methods for predicting whether a protein has a secretory leader as well as the cleavage point for that leader sequence are available. For instance, the methods of McGeoch, *Virus Res.* 3:271-286 (1985) and von Heinje, *Nucleic Acids Res.* 14:4683-4690 (1986) can be used. The accuracy of predicting the cleavage points of known mammalian secretory proteins for each of these methods is in the range of 75-80%. von Heinje, supra. However, the two methods do not always produce the same predicted cleavage point(s) for a given protein.

In the present case, the predicted amino acid sequence of the complete CD33-like polypeptide of the present invention was analyzed by a computer program (PSORT) (Nakai, K. and Kanehisa, M. *Genomics* 14:897-911 (1992)), which is an expert system for predicting the cellular location of a protein based on the amino acid sequence. As part of this computational prediction of localization, the methods of McGeoch and von Heinje are incorporated. The analysis by the PSORT program predicted the cleavage site between amino acids −1 and 1 in SEQ ID NO:2. Thereafter, the complete amino acid sequences were further analyzed by visual inspection, applying a simple form of the (−1,−3) rule of von Heinje. von Heinje, supra. Thus, the leader sequence for the CD33-like protein is predicted to consist of amino acid residues from about −15 to about −1 in SEQ ID NO:2, while the mature CD33-like protein is predicted to consist of residues from about 1 to about 536.

As indicated, nucleic acid molecules of the present invention may be in the form of RNA, such as mRNA, or in the form of DNA, including, for instance, cDNA and genomic DNA obtained by cloning or produced synthetically. The DNA may be double-stranded or single-stranded. Single-stranded DNA may be the coding strand, also known as the sense strand, or it may be the non-coding strand, also referred to as the anti-sense strand.

Isolated nucleic acid molecules of the present invention include DNA molecules comprising an open reading frame (ORF) whose initiation codon is at position 37-39 of the nucleotide sequence shown in FIG. 1A-1C (SEQ ID NO:1) and further include DNA molecules which comprise a sequence substantially different than all or part of the ORF whose initiation codon is at position 37-39 of the nucleotide sequence shown in FIG. 1A-1C (SEQ ID NO:1) but which, due to the degeneracy of the genetic code, still encode the CD33-like protein or a fragment thereof. Of course, the genetic code is well known in the art. Thus, it would be routine for one skilled in the art to generate the degenerate variants described above.

In addition, the invention provides a nucleic acid molecule having a nucleotide sequence related to an extensive portion of SEQ ID NO:1. This cDNA clone is designated HTOBA14R (SEQ ID NO:11).

The sequence of a public EST, having GenBank Accession No. H71235, related to a portion of SEQ ID NO:1 is shown in SEQ ID NO:12. This public EST is 433 nucleotides in length and contains a region of 111 nucleotides having a sequence identical to nucleotides 1899 to 2009 of the sequence shown in SEQ ID NO:1 with the exception of two undisclosed nucleotides at positions 12 and 22 in SEQ ID NO:12. These undisclosed nucleotides are represented by the letter "N".

In another aspect, the invention provides isolated nucleic acid molecules encoding the CD33-like polypeptide having an amino acid sequence encoded by the cDNA of the clone deposited as ATCC Deposit No. 97521 on Apr. 25, 1996. Preferably, the nucleic acid molecule will encode the mature polypeptide encoded by the above-described deposited cDNA.

The invention further provides an isolated nucleic acid molecule having the nucleotide sequence shown in FIG. 1A-1C (SEQ ID NO:1) or the nucleotide sequence of the CD33-like protein gene contained in the above-described deposited cDNA, or a nucleic acid molecule having a sequence complementary to one of the above sequences. In a further embodiment, isolated nucleic acid molecules are provided encoding the full-length CD33-like protein lacking the N-terminal methionine. Such isolated molecules, particularly DNA molecules, are useful as probes for gene mapping by in situ hybridization with chromosomes and for detecting expression of the CD33-like protein gene in human tissue by Northern blot analysis. As described in detail below, detecting enhanced CD33-like protein gene expression in certain tissues is indicative of neoplasia.

The present invention is further directed to fragments of the isolated nucleic acid molecules described herein. By a fragment of an isolated nucleic acid molecule having the nucleotide sequence of the deposited cDNA or the nucleotide sequence shown in FIG. 1A-1C (SEQ ID NO:1) is intended fragments at least about 15 nt, and more preferably at least about 20 nt, still more preferably at least about 30 nt, and even more preferably, at least about 40 nt in length which are useful as diagnostic probes and primers as discussed herein. Of course larger DNA fragments 50, 100, 150, 200, 250, 300, 350, 400, 450, 500, 550, 600, 650, 700, 750, 800, 850, 900, 100, 1050, 1100, 1150, 1200, 1250, 1300, 1350, 1400, 1450, 1500, 1550, 1600, 1650, 1700, 1750, 1800, 1850, 1900, 1950, 2000, or 2010 nt in length are also useful according to the present invention as are fragments corresponding to most, if not all, of the nucleotide sequence of the deposited cDNA or as shown in FIG. 1A-1C (SEQ ID NO:1). By a fragment at least 20 nt in length, for example, is intended fragments which include 20 or more contiguous bases from the nucleotide sequence of the deposited cDNA or the nucleotide sequence as shown in FIG. 1A-1C (SEQ ID NO:1). Since the gene has been deposited and the nucleotide sequence shown in FIG. 1A-1C (SEQ ID NO:1) is provided, generating such DNA fragments would be routine to the skilled artisan. For example, restriction endonuclease cleavage or shearing by sonication could easily be used to generate fragments of various sizes. Alternatively, such fragments could be generated synthetically.

Preferred nucleic acid fragments of the present invention include nucleic acid molecules encoding: a polypeptide comprising the CD33-like protein extracellular domain (amino acid residues from about16 to about 422 in FIG. 1A-1C (amino acids from about 1 to about 407 in SEQ ID NO:2)); a polypeptide comprising the CD33-like protein transmembrane domain (amino acid residues from about 423 to about 464 in FIG. 1A-1C (amino acids from about 408 to about 449 in SEQ ID NO:2)); a polypeptide comprising the CD33-like protein intracellular domain (amino acid residues from about 465 to about 551 in FIG. 1A-1C (amino acids from about 450 to about 536 in SEQ ID NO:2)); a polypeptide comprising the CD33-like protein extracellular and intracellular domain having all or part of the transmembrane region deleted.

In another aspect, the invention provides an isolated nucleic acid molecule comprising a polynucleotide which hybridizes under stringent hybridization conditions to a portion of the polynucleotide in a nucleic acid molecule of the invention described above, for instance, the cDNA clone contained in ATCC Deposit 97521. By "stringent hybridization conditions" is intended overnight incubation at 42° C. in a solution comprising: 50% formamide, 5×SSC (750 mM NaCl, 75 mM tridosium citrate), 50 mM sodium phosphate (pH7.6), 5× Denhardt's solution, 10% dextran sulfate, and 20 µg/ml denatured, sheared salmon sperm DNA, followed by washing the filters in 0.1×SSC at about 65° C. By a polynucleotide which hybridizes to a "portion" of a polynucleotide is intended a polynucleotide (either DNA or RNA) hybridizing to at least about 15 nucleotides (nt), and more preferably at least about 20 nt, still more preferably at least about 30 nt, and even more preferably about 30-70 nt of the reference polynucleotide. These are useful as diagnostic probes and primers as discussed above and in more detail below.

Of course, polynucleotides hybridizing to a larger portion of the reference polynucleotide (e.g., the deposited cDNA clone), for instance, a portion 50-750 nt in length, or even to the entire length of the reference polynucleotide, are also useful as probes according to the present invention, as are polynucleotides corresponding to most, if not all, of the nucleotide sequence of the deposited cDNA or the nucleotide sequence as shown in FIG. 1A-1C (SEQ ID NO:1). By a portion of a polynucleotide of "at least 20 nt in length," for example, is intended 20 or more contiguous nucleotides from the nucleotide sequence of the reference polynucleotide (e.g., the deposited cDNA or the nucleotide sequence as shown in FIG. 1A-1C (SEQ ID NO:1)). As indicated, such portions are useful diagnostically either as a probe according to conventional DNA hybridization techniques or as primers for amplification of a target sequence by the polymerase chain reaction (PCR), as described, for instance, in *Molecular Cloning, A Laboratory Manual,* 2nd. edition, edited by Sambrook, J., Fritsch, E. F. and Maniatis, T., (1989), Cold Spring Harbor Laboratory Press, the entire disclosure of which is hereby incorporated herein by reference.

Of course, a polynucleotide which hybridizes only to a poly A sequence (such as the 3' terminal poly(A) tract of the CD33-like cDNA shown in FIG. 1A-1C (SEQ ID NO:1)), or to a complementary stretch of T (or U) resides, would not be included in a polynucleotide of the invention used to hybridize to a portion of a nucleic acid of the invention, since such a polynucleotide would hybridize to any nucleic acid molecule containing a poly (A) stretch or the complement thereof (e.g., practically any double-stranded cDNA clone).

As indicated, nucleic acid molecules of the present invention which encode the CD33-like polypeptide may include, but are not limited to the coding sequence for the mature polypeptide, by itself; the coding sequence for the mature polypeptide and additional sequences, such as those encoding the about 15 amino acid leader or secretory sequence, such as a pre-, or pro- or prepro-protein sequence; the coding sequence of the mature polypeptide, with or without the aforementioned additional coding sequences, together with additional, non-coding sequences, including for example, but not limited to introns and non-coding 5' and 3' sequences, such as the transcribed, non-translated sequences that play a role in transcription, mRNA processing-including splicing and polyadenylation signals, for example—ribosome binding and stability of mRNA; additional coding sequence which codes for additional amino acids, such as those which provide additional functionalities. Thus, for instance, the sequence encoding the polypeptide may be fused to a marker sequence, such as a sequence encoding a peptide, which facilitates purification of the fused polypeptide. In certain preferred embodiments of this aspect of the invention, the marker sequence is a hexa-histidine peptide, such as the tag provided in a pQE vector (Qiagen, Inc.), among others, many of which are commercially available. As described in Gentz et al., *Proc. Natl. Acad. Sci. USA* 86:821-824 (1989), for instance, hexa-histidine provides for convenient purification of the fusion protein. The HA tag is another peptide useful for purification which corresponds to an epitope derived of influenza hemagglutinin protein, which has been described by Wilson et al., *Cell* 37:767 (1984), for instance. As discussed below, other such fusion proteins include the CD33-like protein fused to Fc at the N- or C-terminus.

The present invention further relates to variants of the nucleic acid molecules of the present invention, which encode fragments, analogs or derivatives of the CD33-like protein. Variants may occur naturally, such as an allelic variant. By an "allelic variant" is intended one of several alternate forms of a gene occupying a given locus on a chromosome of an organism. Lewin, B., ed., *Genes II,* John Wiley & Sons, New York (1985). Non-naturally occurring variants may be produced using art-known mutagenesis techniques.

Such variants include those produced by nucleotide substitutions, deletions or additions. The substitutions, deletions or additions may involve one or more nucleotides. The variants may be altered in coding or non-coding regions or both. Alterations in the coding regions may produce conservative or non-conservative amino acid substitutions, deletions or additions.

Especially preferred among these are silent substitutions, additions and deletions, which do not alter the properties and activities of the CD33-like protein or portions thereof. Also especially preferred in this regard are conservative substitutions.

Further embodiments of the invention include isolated nucleic acid molecules comprising a polynucleotide having a nucleotide sequence at least 95% identical, and more preferably at least 96%, 97%, 98% or 99% identical to: (a) a nucleotide sequence encoding the full-length CD33-like protein having the complete amino acid sequence (including the predicted leader sequence) shown in FIG. 1A-1C (SEQ ID NO:2) or as encoded by the cDNA clone contained in ATCC Deposit No. 97521; (b) a nucleotide sequence encoding the protein having the amino acid sequence in FIG. 1A-1C (SEQ ID NO:2), but lacking the N-terminal methionine; (c) a nucleotide sequence encoding the mature CD33 protein (the full-length polypeptide with the leader removed) having an amino acid sequence shown in FIG. 1A-1C (SEQ ID NO:2) or as encoded by the cDNA clone contained in ATCC Deposit No. 97521; (d) a nucleotide sequence encoding the CD33-like protein extracellular domain having an amino acid sequence shown in FIG. 1A-1C (amino acids from about 1 to about 407 in SEQ ID NO:2) or as encoded by the cDNA clone contained in ATCC Deposit No. 97521; (e) a nucleotide sequence encoding the CD33-like protein intracellular domain having an amino acid sequence shown in FIG. 1A-1C (amino acids from about 450 to about 536 in SEQ ID NO:2) or as encoded by the cDNA clone contained in ATCC Deposit No. 97521; (f) a nucleotide sequence encoding the CD33-like protein transmembrane domain having an amino acid sequence shown in FIG. 1A-1C (amino acids from about 408 to about 449 in SEQ ID NO:2)

or as encoded by the cDNA clone contained in ATCC Deposit No. 97521; (g) a nucleotide sequence encoding the CD33-like protein extracellular domain and intracellular domain (with all or part of the transmembrane domain deleted) having an amino acid sequence shown in FIG. 1A-1C (SEQ ID NO:2) or as encoded by the cDNA clone contained in ATCC Deposit No. 97521; or (h) a nucleotide sequence complementary to any of the nucleotide sequences of (a)-(g).

By a polynucleotide having a nucleotide sequence at least, for example, 95% "identical" to a reference nucleotide sequence encoding a CD33-like protein is intended that the nucleotide sequence of the polynucleotide is identical to the reference sequence except that the polynucleotide sequence may include up to five point mutations per each 100 nucleotides of the reference nucleotide sequence encoding the CD33-like polypeptide. In other words, to obtain a polynucleotide having a nucleotide sequence at least 95% identical to a reference nucleotide sequence, up to 5% of the nucleotides in the reference sequence may be deleted or substituted with another nucleotide, or a number of nucleotides up to 5% of the total nucleotides in the reference sequence may be inserted into the reference sequence. These mutations of the reference sequence may occur at the 5' or 3' terminal positions of the reference nucleotide sequence or anywhere between those terminal positions, interspersed either individually among nucleotides in the reference sequence or in one or more contiguous groups within the reference sequence.

As a practical matter, whether any particular nucleic acid molecule has a nucleotide sequence at least 95%, 97%, 98% or 99% identical to, for instance, the nucleotide sequence shown in FIG. 1A-1C (SEQ ID NO:1) or to the nucleotide sequence of the deposited cDNA clone can be determined conventionally using known computer programs such as the Bestfit® program (Wisconsin Sequence Analysis Package, Version 8 for Unix, Genetics Computer Group, University Research Park, 575 Science Drive, Madison, Wis. 53711). Bestfit® uses the local homology algorithm of Smith and Waterman (Advances in Applied Mathematics 2:482-489, 1981) to find the best segment of homology between two sequences. When using Bestfit® or any other sequence alignment program to determine whether a particular sequence is, for instance, 95% identical to a reference sequence according to the present invention, the parameters are set, of course, such that the percentage of identity is calculated over the full length of the reference nucleotide sequence and that gaps in homology of up to 5% of the total number of nucleotides in the reference sequence are allowed.

The present application is directed to such nucleic acid molecules which are at least 95%, 97%, 98% or 99% identical to a nucleic acid sequence described above irrespective of whether they encode a polypeptide having CD33-like protein activity. This is because, even where a particular nucleic acid molecule does not encode a polypeptide having CD33-like protein activity, one of skill would still know how to use the nucleic acid molecule, for instance, as a hybridization probe or a polymerase chain reaction (PCR) primer. Uses of the nucleic acid molecules of the present invention that do not encode a polypeptide having CD33-like protein activity include, inter alia, (1) isolating the gene encoding the CD33-like protein, or allelic variants thereof from a cDNA library; (2) in situ hybridization (FISH) to metaphase chromosomal spreads to provide precise chromosomal location of the CD33-like gene as described in Verma et al., *Human Chromosomes: a Manual of Basic Techniques,* Pergamon Press, New York (1988); and (3) Northern blot analysis for detecting expression of CD33-like mRNA in specific tissues.

Preferred, however, are nucleic acid molecules which are at least 95%, 97%, 98% or 99% identical to a nucleic acid sequence described above which do, in fact, encode a polypeptide having CD33-like protein activity. By "a polypeptide having CD33-like protein activity" is intended polypeptides exhibiting activity similar, but not necessarily identical, to an activity of the CD33-like polypeptide of the invention as measured in a particular biological assay.

For example, in a solid-phase binding assay, the CD33-like protein of the present invention can mediate sialic acid-dependent adhesion to red blood cells (RBC) in a manner similar to CD33 and sialoadhesin. (This assay is described in detail in Freeman, S. D., et al., *Blood* 85 (8):2005-2012 (1995), the contents of which are incorporated herein by reference). In particular, human red blood cells (RBC) can be modified enzymatically to carry sialic acids in unique linkages (Paulson J C., et al., *Methods Enzymol.* 138:162 (1987)). This provides a useful experimental approach to characterize the specificity of sialic acid-dependent adhesion molecules. Briefly, the assay involves generating Fc-CD33-like protein by polymerase chain reaction amplification of the extracellular portion of the CD33-like protein cDNA described above and cloning into the Fc expression vector, pIG, (Simmons D L: Cloning cell surface molecules by transient expression in mammalian cells, in Hartley D A (ed): *Cellular Interactions in Development-A Practical Approach.* Oxford, UK, IRL, 1993, p 93.) followed by expression in COS-1 cells as described in Freeman, S. D., et al., 85 (8):2005-2012 (1995)). The COS cell supernatants are harvested at about 6 days posttransfection, and the Fc-CD33-like protein purified on protein A Sepharose® as described in Simmons D L, supra.

The solid-phase binding assay involves coating enzyme-linked immunosorbent assay plates the with Fc-CD-33 like protein as described in Kelm, S. et al., *Curr Biol* 4:965 (1994) and adding radiolabeled RBC bearing sialic acid residues in one or of more the structures described in Freeman, S. D. et al., *Blood* 85 (8):2005-2012 (1995) at an appropriate concentration (such as, for example, $4 \times 10^6$ cell/mL). After 30 minutes, nonadherent and loosely adherent cells are removed by washing. The percentage of cells binding in each well is determined as follows: (cpm bound/cpm input)×100. The CD33-like polypeptide of the present invention will bind RBC in a sialic acid-dependent manner.

Thus, by the invention, a "polypeptide having CD33-like protein activity" includes polypeptides that also bind RBC in the above-described assay in a sialic acid-dependent manner. In other words, in a side-by-side comparison, the percentage of RBC binding as described above using the CD33-like protein will be similar (i.e., not more than a 50% difference, and preferably, not more than a 25% difference) to that occurring using a candidate "polypeptide having CD33-like protein activity."

In another embodiment, the above-described binding assay is useful for screening potential antagonist and agonist of CD33-like protein activity. The method involves determining whether a candidate agonist or antagonist (such as an anti-CD33-like protein antibody) enhances or inhibits sialic acid-dependent binding of the CD33-like protein to RBC relative to a standard binding level, i.e., the degree of CD33-like protein binding to RBC in the absence of the candidate agonist or antagonist.

Of course, due to the degeneracy of the genetic code, one of ordinary skill in the art will immediately recognize that large number of the nucleic acid molecules having a nucleotide sequence at least 95%, 97%, 98% or 99% identical to a nucleic acid sequence described above will encode a polypeptide "having CD33-like protein activity." In fact, since degenerate variants all encode the same polypeptide, this will be clear to the skilled artisan even without performing the above-described comparison assay. It will be further recognized in the art that, for such nucleic acid molecules that are not degenerate variants, a reasonable number will also encode a polypeptide having CD33-like protein activity. This is because the skilled artisan is fully aware of amino acid substitutions that are either less likely or not likely to significantly effect protein function (e.g., replacing one aliphatic amino acid with a second aliphatic amino acid).

For example, guidance concerning how to make phenotypically silent amino acid substitutions is provided in Bowie, J. U., et al., "Deciphering the Message in Protein Sequences: Tolerance to Amino Acid Substitutions," *Science* 247:1306-1310 (1990), wherein the authors indicate that there are two main approaches for studying the tolerance of an amino acid sequence to change. The first method relies on the process of evolution, in which mutations are either accepted or rejected by natural selection. The second approach uses genetic engineering to introduce amino acid changes at specific positions of a cloned gene and selects or screens to identify sequences that maintain functionality. As the authors state, these studies have revealed that proteins are surprisingly tolerant of amino acid substitutions. The authors further indicate which amino acid changes are likely to be permissive at a certain position of the protein. For example, most buried amino acid residues require nonpolar side chains, whereas few features of surface side chains are generally conserved. Other such phenotypically silent substitutions are described in Bowie, J. U. et al., supra, and the references cited therein.

Vectors and Host Cells

The present invention also relates to vectors which include the isolated DNA molecules of the present invention, host cells which are genetically engineered with the recombinant vectors, and the production of CD33-like polypeptides or fragments thereof by recombinant techniques.

Recombinant constructs may be introduced into host cells using well known techniques such as infection, transduction, transfection, transvection and transformation. The vector may be, for example, a plasmid, viral or retroviral vector. Retroviral vectors may be replication competent or replication defective. In the latter case, retroviral propagation generally will occur only in complementing host cells.

The polynucleotides may be joined to a vector containing a selectable marker for propagation in a host. Generally, a plasmid vector is introduced in a precipitate, such as a calcium phosphate precipitate, or in a complex with a charged lipid. If the vector is a virus, it may be packaged in vitro using an appropriate packaging cell line and then transfected into host cells.

Preferred are vectors comprising cis-acting control regions to the polynucleotide of interest. Appropriate trans-acting factors either are supplied by the host, supplied by a complementing vector or supplied by the vector itself upon introduction into the host.

In certain preferred embodiments in this regard, the vectors provide for specific expression, which be inducible and/or cell type-specific. Particularly preferred among inducible vectors are vectors that can be induced for expression by environmental factors that are easy to manipulate, such as temperature and nutrient additives.

Expression vectors useful in the present invention include chromosomal-, episomal- and virus-derived vectors e.g., vectors derived from bacterial plasmids, bacteriophage, yeast episomes, yeast chromosomal elements, viruses such as baculoviruses, papova viruses, vaccinia viruses, adenoviruses, fowl pox viruses, pseudorabies viruses and retroviruses, and vectors derived from combinations thereof, such as those derived from plasmid and bacteriophage genetic elements, such as cosmids and phagemids.

The DNA insert should be operatively linked to an appropriate promoter, such as the phage lambda PL promoter, the *E. coli* lac, trp and tac promoters, the SV40 early and late promoters and promoters of retroviral LTRs, to name a few. Other suitable promoters will be known to the skilled artisan. The expression constructs will contain sites for transcription initiation, termination, and, in the transcribed region, a ribosome binding site for translation. The coding portion of the mature transcripts expressed by the constructs will include a translation initiating AUG at the beginning and a termination codon appropriately positioned at the end of the polypeptide to be translated.

As indicated, the expression vectors will preferably contain selectable markers. Such markers include dihydrofolate reductase or neomycin resistance for eukaryotic cell culture and tetracycline or ampicillin resistance for culturing in *E. coli* and other bacteria. Representative examples of appropriate hosts include bacterial cells, such as *E. coli,* Streptomyces and *Salmonella typhimurium,* fungal cells, such as yeast; insect cells such as *Drosophila* S2 and *Spodoptera* Sf9; animal cells such as CHO, COS and Bowes melanoma; and plant cells. Appropriate culture mediums and conditions for the above-described host cells are known in the art.

Among vectors preferred for use in bacteria are pQE70, pQE60 and pQE-9, available from Qiagen; pBS vectors, Phagescript vectors, Bluescript® vectors, pNH8A, pNH16a, pNH18A, pNH46A, available from Stratagene; and ptrc99a, pKK223-3, pKK233-3, pDR540, pRIT5 available from Pharmacia. Among preferred eukaryotic vectors are pWL-NEO, pSV2CAT, pOG44, pXT1 and pSG available from Stratagene; and pSVK3, pBPV, pMSG and pSVL available from Pharmacia. Other suitable vectors will be readily apparent to the skilled artisan.

Among known bacterial promoters for use in the present invention include *E. coli* lacI and lacZ promoters, the T3 and T7 promoters, the gpt promoter, the lambda PR, PL promoters and the trp promoter. Suitable eukaryotic promoters include the CMV immediate early promoter, the HSV thymidine kinase promoter, the early and late SV40 promoters, the promoters of retroviral LTRs, such as those of the Rous sarcoma virus ("RSV"), and metallothionein promoters, such as the mouse metallothionein-I promoter.

Introduction of the construct into the host cell can be effected by calcium phosphate transfection, DEAE-dextran mediated transfection, cationic lipid-mediated transfection, electroporation, transduction, infection or other methods. Such methods are described in many standard laboratory manuals, such as Davis et al., *Basic Methods in Molecular Biology* (1986).

Transcription of the DNA encoding the polypeptides of the present invention by higher eukaryotes may be increased by inserting an enhancer sequence into the vector. Enhancers are cis-acting elements of DNA, usually about from 10 to 300 bp that act to increase transcriptional activity of a promoter in a given host cell-type. Examples of enhancers include the SV40 enhancer, which is located on the late side of the replication origin at bp 100 to 270, the cytomegalovirus early promoter enhancer, the polyoma enhancer on the late side of the replication origin, and adenovirus enhancers.

For secretion of the translated protein into the lumen of the endoplasmic reticulum, into the periplasmic space or into the extracellular environment, appropriate secretion signals may be incorporated into the expressed polypeptide. The signals may be endogenous to the polypeptide or they may be heterologous signals.

The polypeptide may be expressed in a modified form, such as a fusion protein, and may include not only secretion signals but also additional heterologous functional regions. Thus, for instance, a region of additional amino acids, particularly charged amino acids, may be added to the N-terminus of the polypeptide to improve stability and persistence in the host cell, during purification or during subsequent handling and storage. Also, peptide moieties may be added to the polypeptide to facilitate purification. Such regions may be removed prior to final preparation of the polypeptide. The addition of peptide moieties to polypeptides to engender secretion or excretion, to improve stability and to facilitate purification, among others, are familiar and routine techniques in the art. A preferred fusion protein comprises a heterologous region from immunoglobulin that is useful to solubilize proteins. For example, EPA 0 464 533 (Canadian counterpart 2045869) discloses fusion proteins comprising various portions of constant region of immunoglobin molecules together with another human protein or part thereof. In many cases, the Fc part in a fusion protein is thoroughly advantageous for use in therapy and diagnosis and thus results, for example, in improved pharmacokinetic properties (EPA 0 232 262). On the other hand, for some uses it would be desirable to be able to delete the Fc part after the fusion protein has been expressed, detected and purified in the advantageous manner described. This is the case when the Fc portion proves to be a hindrance to use in therapy and diagnosis, for example when the fusion protein is to be used as an antigen for immunizations. In drug discovery, for example, human proteins, such as the hIL5-receptor, have been fused with Fc portions for the purpose of high-throughput screening assays to identify antagonists of hIL-5. See, D. Bennett et al., *J. of Molec. Recognition* 8:52-58 (1995) and K. Johanson et al., *J. Biol. Chem.* 270:9459-9471 (1995).

The CD33-like protein can be recovered and purified from recombinant cell cultures by well-known methods including ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. Most preferably, high performance liquid chromatography ("HPLC") is employed for purification.

Polypeptides of the present invention include naturally purified products, products of chemical synthetic procedures, and products produced by recombinant techniques from a prokaryotic or eukaryotic host, including, for example, bacterial, yeast, higher plant, insect and mammalian cells. Depending upon the host employed in a recombinant production procedure, the polypeptides of the present invention may be glycosylated or may be non-glycosylated. In addition, polypeptides of the invention may also include an initial modified methionine residue, in some cases as a result of host-mediated processes.

CD33-Like Polypeptides and Fragments

The invention further provides an isolated CD33-like polypeptide having the amino acid sequence encoded by the deposited cDNA, or the amino acid sequence as shown in FIG. 1A-1C (SEQ ID NO:2), or a peptide or polypeptide comprising a portion of the above polypeptides. The terms "peptide" and "oligopeptide" are considered synonymous (as is commonly recognized) and each term can be used interchangeably as the context requires to indicate a chain of at least two amino acids coupled by peptidyl linkages. The word "polypeptide" is used herein for chains containing more than ten amino acid residues. All oligopeptide and polypeptide formulas or sequences herein are written from left to right and in the direction from amino terminus to carboxy terminus.

It will be recognized in the art that some amino acid sequences of the CD33-like polypeptide can be varied without significant effect on the structure or function of the protein. If such differences in sequence are contemplated, it should be remembered that there will be critical areas on the protein which determine activity.

Thus, the invention further includes variations of the CD33-like polypeptide which show substantial CD33-like polypeptide activity or which include regions of CD33-like protein such as the protein portions discussed below. Such mutants include deletions, insertions, inversions, repeats, and type substitutions. As indicated above, guidance concerning which amino acid changes are likely to be phenotypically silent can be found in Bowie, J. U., et al., "Deciphering the Message in Protein Sequences: Tolerance to Amino Acid Substitutions," *Science* 247:1306-1310 (1990).

Thus, the fragment, derivative or analog of the polypeptide of SEQ ID NO:2, or that encoded by the deposited cDNA, may be (i) one in which one or more of the amino acid residues are substituted with a conserved or non-conserved amino acid residue (preferably a conserved amino acid residue) and such substituted amino acid residue may or may not be one encoded by the genetic code, or (ii) one in which one or more of the amino acid residues includes a substituent group, or (iii) one in which the mature polypeptide is fused with another compound, such as a compound to increase the half-life of the polypeptide (for example, polyethylene glycol), or (iv) one in which the additional amino acids are fused to the mature polypeptide, such as an IgG Fc fusion region peptide or leader or secretory sequence or a sequence which is employed for purification of the mature polypeptide or a proprotein sequence. Such fragments, derivatives and analogs are deemed to be within the scope of those skilled in the art from the teachings herein.

Of particular interest are substitutions of charged amino acids with another charged amino acid and with neutral or negatively charged amino acids. The latter results in proteins with reduced positive charge to improve the characteristics of the CD33-like protein. The prevention of aggregation is highly desirable. Aggregation of proteins not only results in a loss of activity but can also be problematic when preparing pharmaceutical formulations, because they can be immunogenic. (Pinckard et al., *Clin. Exp. Immunol.* 2:331-340 (1967); Robbins et al., *Diabetes* 36:838-845 (1987); Cleland et al. *Crit. Rev. Therapeutic Drug Carrier Systems* 10:307-377 (1993)).

As indicated, changes are preferably of a minor nature, such as conservative amino acid substitutions that do not significantly affect the folding or activity of the protein (see Table 1).

TABLE 1

Conservative Amino Acid Substitutions.

| | |
|---|---|
| Aromatic | Phenylalanine |
| | Tryptophan |
| | Tyrosine |
| Hydrophobic | Leucine |
| | Isoleucine |
| | Valine |
| Polar | Glutamine |
| | Asparagine |
| Basic | Arginine |
| | Lysine |
| | Histidine |
| Acidic | Aspartic Acid |
| | Glutamic Acid |
| Small | Alanine |
| | Serine |
| | Threonine |
| | Methionine |
| | Glycine |

Amino acids in the CD33-like protein of the present invention that are essential for function can be identified by methods known in the art, such as site-directed mutagenesis or alanine-scanning mutagenesis (Cunningham and Wells, *Science* 244:1081-1085 (1989)). The latter procedure introduces single alanine mutations at every residue in the molecule. Sites that are critical for ligand binding can also be determined by structural analysis such as crystallization, nuclear magnetic resonance or photoaffinity labeling (Smith et al., *J. Mol. Biol.* 224:899-904 (1992) and de Vos et al., *Science* 255:306-312 (1992)).

The polypeptides of the present invention are preferably provided in an isolated form. By "isolated polypeptide" is intended a polypeptide removed from its native environment. Thus, a polypeptide produced and/or contained within a recombinant host cell is considered isolated for purposes of the present invention. Also intended as an "isolated polypeptide" are polypeptides that have been purified, partially or substantially, from a recombinant host cell. For example, a recombinantly produced version of the CD33-like protein polypeptide can be substantially purified by the one-step method described in Smith and Johnson, *Gene* 67:31-40 (1988).

The polypeptides of the present invention include the polypeptide encoded by the deposited cDNA including the leader; the mature polypeptide encoded by the deposited cDNA minus the leader (i.e., the mature protein); a polypeptide comprising amino acids about −15 to about 536 in SEQ ID NO:2; a polypeptide comprising amino acids about −14 to about 536 in SEQ ID NO:2; a polypeptide comprising amino acids about 1 to about 536 in SEQ ID NO:2; a polypeptide comprising amino acids about 1 to about 407 in SEQ ID NO:2; a polypeptide comprising amino acids about 408 to about 449 in SEQ ID NO:2; a polypeptide comprising amino acids about 450 to about 536 in SEQ ID NO:2; a polypeptide comprising the CD33-like polypeptide extracellular and intracellular domains with all or part of the transmembrane domain deleted; as well as polypeptides which are at least 95% identical, more preferably at least 96%, 97%, 98% or 99% identical to the polypeptide encoded by the deposited cDNA, to the polypeptide of SEQ ID NO:2, and also include portions of such polypeptides with at least 30 amino acids and more preferably at least 50 amino acids.

By a polypeptide having an amino acid sequence at least, for example, 95% "identical" to a reference amino acid sequence of a CD33-like polypeptide is intended that the amino acid sequence of the polypeptide is identical to the reference sequence except that the polypeptide sequence may include up to five amino acid alterations per each 100 amino acids of the reference amino acid of the CD33-like polypeptide. In other words, to obtain a polypeptide having an amino acid sequence at least 95% identical to a reference amino acid sequence, up to 5% of the amino acid residues in the reference sequence may be deleted or substituted with another amino acid, or a number of amino acids up to 5% of the total amino acid residues in the reference sequence may be inserted into the reference sequence. These alterations of the reference sequence may occur at the amino or carboxy terminal positions of the reference amino acid sequence or anywhere between those terminal positions, interspersed either individually among residues in the reference sequence or in one or more contiguous groups within the reference sequence.

As a practical matter, whether any particular polypeptide is at least 95%, 97%, 98% or 99% identical to, for instance, the amino acid sequence shown in FIG. 1A-1C (SEQ ID NO:2) or to the amino acid sequence encoded by deposited cDNA clone or a portion thereof can be determined conventionally using known computer programs such the Bestfit® program (Wisconsin Sequence Analysis Package, Version 8 for Unix, Genetics Computer Group, University Research Park, 575 Science Drive, Madison, Wis. 53711). When using Bestfit® or any other sequence alignment program to determine whether a particular sequence is, for instance, 95% identical to a reference sequence according to the present invention, the parameters are set, of course, such that the percentage of identity is calculated over the full length of the reference amino acid sequence and that gaps in homology of up to 5% of the total number of amino acid residues in the reference sequence are allowed.

The polypeptide of the present invention are useful as a molecular weight marker on SDS-PAGE gels or on molecular sieve gel filtration columns using methods well known to those of skill in the art.

In another aspect, the invention provides a peptide or polypeptide comprising an epitope-bearing portion of a polypeptide of the invention. The epitope of this polypeptide portion is an immunogenic or antigenic epitope of a polypeptide of the invention. An "immunogenic epitope" is defined as a part of a protein that elicits an antibody response when the whole protein is the immunogen. These immunogenic epitopes are believed to be confined to a few loci on the molecule. On the other hand, a region of a protein molecule to which an antibody can bind is defined as an "antigenic epitope." The number of immunogenic epitopes of a protein generally is less than the number of antigenic epitopes. See, for instance, Geysen, H. M. et al., *Proc. Natl. Acad. Sci. USA* 81:3998-4002 (1984).

As to the selection of peptides or polypeptides bearing an antigenic epitope (i.e., that contain a region of a protein molecule to which an antibody can bind), it is well known in that art that relatively short synthetic peptides that mimic part of a protein sequence are routinely capable of eliciting an antiserum that reacts with the partially mimicked protein. See, for instance, Sutcliffe, J. G. et al., *Science* 219:660-666 (1984). Peptides capable of eliciting protein-reactive sera are frequently represented in the primary sequence of a protein, can be characterized by a set of simple chemical rules, and are confined neither to immunodominant regions of intact proteins (i.e., immunogenic epitopes) nor to the amino or carboxyl terminals. Peptides that are extremely hydrophobic and those of six or fewer residues generally are ineffective at inducing antibodies that bind to the mimicked protein; longer, soluble peptides, especially those containing proline residues, usually are effective. Sutcliffe et al., supra, at 661. For instance, 18 of 20 peptides designed according to these guidelines, containing 8-39 residues covering 75% of the sequence of the influenza virus hemagglutinin HA1 polypeptide chain, induced antibodies that reacted with the HA1 protein or intact virus; and 12/12 peptides from the MuLV polymerase and 18/18 from the rabies glycoprotein induced antibodies that precipitated the respective proteins.

Antigenic epitope-bearing peptides and polypeptides of the invention are therefore useful to raise antibodies, including monoclonal antibodies, that bind specifically to a polypeptide of the invention. Thus, a high proportion of hybridomas obtained by fusion of spleen cells from donors immunized with an antigen epitope-bearing peptide generally secrete antibody reactive with the native protein. Sutcliffe et al., supra, at 663. The antibodies raised by antigenic epitope-bearing peptides or polypeptides are useful to detect the mimicked protein, and antibodies to different peptides may be used for tracking the fate of various regions of a protein precursor which undergoes posttranslation processing. The peptides and anti-peptide antibodies may be used in a variety of qualitative or quantitative assays for the mimicked protein, for instance in competition assays since it has been shown that even short peptides (e.g., about 9 amino acids) can bind and displace the larger peptides in immunoprecipitation assays. See, for instance, Wilson, I. A. et al., Cell 37:767-778 at 777 (1984). The anti-peptide antibodies of the invention also are useful for purification of the mimicked protein, for instance, by adsorption chromatography using methods well known in the art.

Antigenic epitope-bearing peptides and polypeptides of the invention designed according to the above guidelines preferably contain a sequence of at least seven, more preferably at least nine and most preferably between about 15 to about 30 amino acids contained within the amino acid sequence of a polypeptide of the invention. However, peptides or polypeptides comprising a larger portion of an amino acid sequence of a polypeptide of the invention, containing about 30 to about 50 amino acids, or any length up to and including the entire amino acid sequence of a polypeptide of the invention, also are considered epitope-bearing peptides or polypeptides of the invention and also are useful for inducing antibodies that react with the mimicked protein. Preferably, the amino acid sequence of the epitope-bearing peptide is selected to provide substantial solubility in aqueous solvents (i.e., the sequence includes relatively hydrophilic residues and highly hydrophobic sequences are preferably avoided); and sequences containing proline residues are particularly preferred.

The epitope-bearing peptides and polypeptides of the invention may be produced by any conventional means for making peptides or polypeptides including recombinant means using nucleic acid molecules of the invention. For instance, a short epitope-bearing amino acid sequence may be fused to a larger polypeptide which acts as a carrier during recombinant production and purification, as well as during immunization to produce anti-peptide antibodies. Epitope-bearing peptides also may be synthesized using known methods of chemical synthesis. For instance, Houghten has described a simple method for synthesis of large numbers of peptides, such as 10-20 mg of 248 different 13 residue peptides representing single amino acid variants of a segment of the HA1 polypeptide which were prepared and characterized (by ELISA-type binding studies) in less than four weeks. Houghten, R. A., Proc. Natl. Acad. Sci. USA 82:5131-5135 (1985). This "Simultaneous Multiple Peptide Synthesis (SMPS)" process is further described in U.S. Pat. No. 4,631,211 to Houghten et al. (1986). In this procedure the individual resins for the solid-phase synthesis of various peptides are contained in separate solvent-permeable packets, enabling the optimal use of the many identical repetitive steps involved in solid-phase methods. A completely manual procedure allows 500-1000 or more syntheses to be conducted simultaneously. Houghten et al., supra, at 5134.

Epitope-bearing peptides and polypeptides of the invention are used to induce antibodies according to methods well known in the art. See, for instance, Sutcliffe et al., supra; Wilson et al., supra; Chow, M. et al., Proc. Natl. Acad. Sci. USA 82:910-914; and Bittle, F. J. et al., J. Gen. Virol. 66:2347-2354 (1985). Generally, animals may be immunized with free peptide; however, anti-peptide antibody titer may be boosted by coupling of the peptide to a macromolecular carrier, such as keyhole limpet hemacyanin (KLH) or tetanus toxoid. For instance, peptides containing cysteine may be coupled to carrier using a linker such as m-maleimidobenzoyl-N-hydroxysuccinimide ester (MBS), while other peptides may be coupled to carrier using a more general linking agent such as glutaraldehyde. Animals such as rabbits, rats and mice are immunized with either free or carrier-coupled peptides, for instance, by intraperitoneal and/or intradermal injection of emulsions containing about 100 µg peptide or carrier protein and Freund's adjuvant. Several booster injections may be needed, for instance, at intervals of about two weeks, to provide a useful titer of anti-peptide antibody which can be detected, for example, by ELISA assay using free peptide adsorbed to a solid surface. The titer of anti-peptide antibodies in serum from an immunized animal may be increased by selection of anti-peptide antibodies, for instance, by adsorption to the peptide on a solid support and elution of the selected antibodies according to methods well known in the art.

Immunogenic epitope-bearing peptides of the invention, i.e., those parts of a protein that elicit an antibody response when the whole protein is the immunogen, are identified according to methods known in the art. For instance, Geysen et al., 1984, supra, discloses a procedure for rapid concurrent synthesis on solid supports of hundreds of peptides of sufficient purity to react in an enzyme-linked immunosorbent assay. Interaction of synthesized peptides with antibodies is then easily detected without removing them from the support. In this manner a peptide bearing an immunogenic epitope of a desired protein may be identified routinely by one of ordinary skill in the art. For instance, the immunologically important epitope in the coat protein of foot-and-mouth disease virus was located by Geysen et al. with a resolution of seven amino acids by synthesis of an overlapping set of all 208 possible hexapeptides covering the entire 213 amino acid sequence of the protein. Then, a complete replacement set of peptides in which all 20 amino acids were substituted in turn at every position within the epitope were synthesized, and the particular amino acids conferring specificity for the reaction with antibody were determined. Thus, peptide analogs of the epitope-bearing peptides of the invention can be made routinely by this method. U.S. Pat. No. 4,708,781 to Geysen (1987) further describes this method of identifying a peptide bearing an immunogenic epitope of a desired protein.

Further still, U.S. Pat. No. 5,194,392 to Geysen (1990) describes a general method of detecting or determining the sequence of monomers (amino acids or other compounds) which is a topological equivalent of the epitope (i.e., a "mimotope") which is complementary to a particular paratope (antigen binding site) of an antibody of interest. More generally, U.S. Pat. No. 4,433,092 to Geysen (1989) describes a method of detecting or determining a sequence of monomers which is a topographical equivalent of a ligand which is complementary to the ligand binding site of a particular receptor of interest. Similarly, U.S. Pat. No. 5,480,971 to Houghten, R. A. et al. (1996) on Peralkylated Oligopeptide Mixtures discloses linear $C_1$-$C_7$-alkyl peralkylated oligopeptides and sets and libraries of such peptides, as well as methods for using such oligopeptide sets and libraries for determining the sequence of a peralkylated oligopeptide that preferentially binds to an acceptor molecule of interest. Thus, non-peptide analogs of the epitope-bearing peptides of the invention also can be made routinely by these methods.

The present inventors have discovered that the CD33-like protein is a 551 residue protein exhibiting three main structural domains. First, the extracellular domain (which includes the ligand binding domain) was identified within residues from about16 to about 422 in FIG. 1A-1C (amino acids from about 1 to about 407 in SEQ ID NO:2). The mature extracellular domain has been predicted by the inventors as being about 407 amino acids in length with a molecular weight of about 45 kDa. Second, the transmembrane domain was identified within residues from about 423 to about 464 in FIG. 1A-1C (amino acids from about 408 to about 449 in SEQ ID NO:2). Third, the intracellular domain was identified within residues from about 465 to about 551 in FIG. 1A-1C (amino acids from about 450 to about 536 in SEQ ID NO:2). Thus, the invention further provides preferred CD33-like protein fragments comprising a polypeptide selected from: the mature CD33-like protein; the CD33-like protein extracellular domain; the CD33-like protein transmembrane domain; the CD33-like protein intracellular domain; or the CD33-like protein extracellular domain and intracellular domain with part or all of the transmembrane domain deleted. Methods for producing such CD33-like protein fragments are described above.

The extracellular domains of receptors can be combined with parts of the constant domain of immunoglobulins (IgG), resulting in chimeric polypeptides. These fusion proteins often show an increased half-life time in vivo. This has been shown, e.g., for chimeric proteins consisting of the first two domains of the human CD4 polypeptide and various domains of the constant regions of the heavy or light chains of mammalian immunoglobulins (European Patent Application Publication No. 394 827; Traunecker et al., Nature 331:84-86 (1988)). Fusion proteins that have disulfide-linked dimeric structure due to the IgG part can also be more efficient in binding and neutralizing the ligands than the monomeric extracellular domains alone (Fountoulakis et al., J. Biochem. 270:3958-3964 (1995)).

As described in detail below, the polypeptides of the present invention and fragments thereof can be used to raise polyclonal and monoclonal antibodies, which are useful in diagnostic assays for detecting CD33-like protein expression as described below or as agonists and antagonists capable of enhancing or inhibiting CD33-like protein function. Further, such polypeptides can be used in the yeast two-hybrid system to "capture" CD33-like protein binding proteins which are also candidate agonist and antagonist according to the present invention. The yeast two hybrid system is described in Fields and Song, Nature 340:245-246 (1989).

The entire disclosure of each document cited in this section on "CD33-Like Polypeptides and Fragments" is hereby incorporated herein by reference.

Cancer and Inflammatory Disease Diagnosis and Prognosis

It is believed that certain tissues in mammals with cancer or inflammatory disease contain significantly greater CD33-like protein gene copy number and express significantly enhanced levels of the CD33-like protein and mRNA encoding the CD33-like protein when compared to a corresponding "standard" mammal, i.e., a mammal of the same species not having the cancer or inflammatory disease. Enhanced levels of the CD33-like protein will be detected in certain body fluids (e.g., sera, plasma, urine, synovial and spinal fluid) from mammals with cancer or inflammatory disease when compared to sera from mammals of the same species not having the cancer or inflammatory disease. Thus, the invention provides a method useful during tumor or inflammatory disease diagnosis, which involves assaying the expression level of the gene encoding the CD33-like protein or the gene copy number in mammalian cells or body fluid and comparing the gene expression level or gene copy number with a standard CD33-like protein gene expression level or gene copy number, whereby an increase in the gene expression level or gene copy number over the standard is indicative of certain tumors or inflammatory disease.

Where a tumor or inflammatory disease diagnosis has already been made according to conventional methods, the present invention is useful as a prognostic indicator. For example, samples of bone marrow or peripheral blood can be obtained from patients diagnosed previously with leukemia to obtain leukemic blasts for examination of the CD33-like protein expression using anti-CD33-like protein monoclonal antibodies. Because the level of differentiation of normal myeloid cells is believed to be reflected by the concentration of the CD33-like protein antigen expressed, samples can be categorized as CD33-bright (immature) versus CD33-dull (mature). Patients whose leukemic blasts display the CD33-like protein antigen in an amount associated with immature myeloid cells will experience a worse clinical outcome than patients with leukemic blasts expressing a phenotype associated with more mature cells (i.e., a relatively lower CD33-like protein expression level).

By "assaying the expression level of the gene encoding the CD33-like protein" is intended qualitatively or quantitatively measuring or estimating the level of the CD33-like protein or the level of the mRNA encoding the CD33-like protein in a first biological sample either directly (e.g., by determining or estimating absolute protein level or mRNA level) or relatively (e.g., by comparing to the CD33-like protein level or mRNA level in a second biological sample). By "assaying the copy number of the gene encoding the CD33-like protein" is intended qualitatively or quantitatively measuring or estimating the gene copy number in a first biological sample either directly (e.g., by determining or estimating absolute gene copy number) or relatively (e.g., by comparing to the CD33-like protein gene copy number in a second biological sample).

Preferably, the CD33-like-protein level, mRNA level, or gene copy number in the first biological sample is measured or estimated and compared to a standard CD33-like protein level, mRNA level, or gene copy number, the standard being taken from a second biological sample obtained from an individual not having the cancer or inflammatory disease. Alternatively, where the method is used as a prognostic indicator, both the first and second biological samples can be taken from individuals having the cancer or inflammatory disease and the relative expression levels or copy number will be measured to determine prognosis. As will be appreciated in the art, once a standard CD33-like protein level, mRNA level, or gene copy number is known, it can be used repeatedly as a standard for comparison.

By "biological sample" is intended any biological sample obtained from an individual, cell line, tissue culture, or other source which contains CD33-like protein or mRNA. Biological samples include mammalian body fluids (such as sera, plasma, urine, synovial fluid and spinal fluid) which contain secreted mature CD33-like protein or its soluble extracellular domain, and eosinophils, spleen tissue, monocytes, neutrophils, tonsils, and bone marrow. Methods for obtaining tissue biopsies and body fluids from mammals are well known in the art. Where the biological sample is to include mRNA, a tissue biopsy is the preferred source.

The present invention is useful for detecting cancer and inflammatory disease in mammals. In particular the invention is useful during diagnosis or prognosis of the following types of cancers and inflammatory diseases in mammals: metastatic tumors, leukemias, lymphomas, arthritis, and allergical diseases. Preferred mammals include monkeys, apes, cats, dogs, cows, pigs, horses, rabbits and humans. Particularly preferred are humans.

Total cellular RNA can be isolated from a biological sample using any suitable technique such as the single-step guanidinium-thiocyanate-phenol-chloroform method described in Chomczynski and Sacchi, *Anal. Biochem.* 162: 156-159 (1987). Levels of mRNA encoding the CD33-like protein are then assayed using any appropriate method. These include Northern blot analysis, S1 nuclease mapping, the polymerase chain reaction (PCR), reverse transcription in combination with the polymerase chain reaction (RT-PCR), and reverse transcription in combination with the ligase chain reaction (RT-LCR).

Northern blot analysis can be performed as described in Harada et al., *Cell* 63:303-312 (1990). Briefly, total RNA is prepared from a biological sample as described above. For the Northern blot, the RNA is denatured in an appropriate buffer (such as glyoxal/dimethyl sulfoxide/sodium phosphate buffer), subjected to agarose gel electrophoresis, and transferred onto a nitrocellulose filter. After the RNAs have been linked to the filter by a UV linker, the filter is prehybridized in a solution containing formamide, SSC, Denhardt's solution, denatured salmon sperm, SDS, and sodium phosphate buffer. CD33-like protein cDNA labeled according to any appropriate method (such as the $^{32}$P-multiprimed DNA labeling system (Amersham)) is used as a probe. After hybridization overnight, the filter is washed and exposed to x-ray film. cDNA for use as probe according to the present invention is described in the sections above and will preferably be at least 15 bp in length.

S1 mapping can be performed as described in Fujita et al., *Cell* 49:357-367 (1987). To prepare probe DNA for use in S1 mapping, the sense strand of above-described cDNA is used as a template to synthesize labeled antisense DNA. The antisense DNA can then be digested using an appropriate restriction endonuclease to generate further DNA probes of a desired length. Such antisense probes are useful for visualizing protected bands corresponding to the target mRNA (i.e., mRNA encoding the CD33-like protein). Northern blot analysis can be performed as described above.

Preferably, levels of mRNA encoding the CD33-like protein are assayed using the RT-PCR method described in Makino et al., *Technique* 2:295-301 (1990). By this method, the radioactivities of the "amplicons" in the polyacrylamide gel bands are linearly related to the initial concentration of the target mRNA. Briefly, this method involves adding total RNA isolated from a biological sample in a reaction mixture containing a RT primer and appropriate buffer. After incubating for primer annealing, the mixture can be supplemented with a RT buffer, dNTPs, DTT, RNase inhibitor and reverse transcriptase. After incubation to achieve reverse transcription of the RNA, the RT products are then subject to PCR using labeled primers. Alternatively, rather than labeling the primers, a labeled dNTP can be included in the PCR reaction mixture. PCR amplification can be performed in a DNA thermal cycler according to conventional techniques. After a suitable number of rounds to achieve amplification, the PCR reaction mixture is electrophoresed on a polyacrylamide gel. After drying the gel, the radioactivity of the appropriate bands (corresponding to the mRNA encoding the CD33-like protein)) is quantified using an imaging analyzer. RT and PCR reaction ingredients and conditions, reagent and gel concentrations, and labeling methods are well known in the art. Variations on the RT-PCR method will be apparent to the skilled artisan.

Any set of oligonucleotide primers which will amplify reverse transcribed target mRNA can be used and can be designed as described in the sections above.

Assaying CD33-like protein gene copy number can occur according to any known technique, such as for example, in situ hybridization of tissue samples with a cDNA probe described above.

Assaying CD33-like protein levels in a biological sample can occur using any art-known method. Preferred for assaying CD33-like protein levels in a biological sample are antibody-based techniques. For example, CD33-like protein expression in tissues can be studied with classical immunohistological methods. In these, the specific recognition is provided by the primary antibody (polyclonal or monoclonal) but the secondary detection system can utilize fluorescent, enzyme, or other conjugated secondary antibodies. As a result, an immunohistological staining of tissue section for pathological examination is obtained. Tissues can also be extracted, e.g., with urea and neutral detergent, for the liberation of CD33-like protein for Western-blot or dot/slot assay (Jalkanen, M., et al., *J. Cell. Biol.* 101:976-985 (1985)); Jalkanen, M., et al., *J. Cell. Biol.* 105:3087-3096 (1987)). In this technique, which is based on the use of cationic solid phases, quantitation of CD33-like protein can be accomplished using isolated CD33-like protein as a standard. This technique can also be applied to body fluids. With these samples, a molar concentration of CD33-like protein will aid to set standard values of CD33-like protein content for different body fluids, like serum, plasma, urine, spinal fluid, etc. The normal appearance of CD33-like protein amounts can then be set using values from healthy individuals, which can be compared to those obtained from a test subject.

Other antibody-based methods useful for detecting CD33-like protein gene expression include immunoassays, such as the enzyme linked immunosorbent assay (ELISA) and the radioimmunoassay (RIA). For example, a CD33-like protein-specific monoclonal antibody can be used both as an immunoabsorbent and as an enzyme-labeled probe(to detect and quantify the CD33-like protein. The amount of CD33-like protein present in the sample can be calculated by reference to the amount present in a standard preparation using a linear regression computer algorithm. Such an ELISA for detecting a tumor antigen is described in Iacobelli et al., *Breast Cancer Research and Treatment* 11:19-30 (1988). In another ELISA assay, two distinct specific monoclonal antibodies can be used to detect CD33-like protein in a body fluid. In this assay, one of the antibodies is used as the immunoabsorbent and the other as the enzyme-labeled probe.

The above techniques may be conducted essentially as a "one-step" or "two-step" assay. The "one-step" assay involves contacting CD33-like protein with immobilized antibody and, without washing, contacting the mixture with the labeled antibody. The "two-step" assay involves washing before contacting the mixture with the labeled antibody. Other conventional methods may also be employed as suitable. It is usually desirable to immobilize one component of the assay system on a support, thereby allowing other components of the system to be brought into contact with the component and readily removed from the sample.

Suitable enzyme labels include, for example, those from the oxidase group, which catalyze the production of hydrogen peroxide by reacting with substrate. Glucose oxidase is particularly preferred as it has good stability and its substrate (glucose) is readily available. Activity of an oxidase label may be assayed by measuring the concentration of hydrogen peroxide formed by the enzyme-labeled antibody/substrate reaction. Besides enzymes, other suitable labels include radioisotopes, such as iodine ($^{125}I$, $^{121}I$), carbon ($^{14}C$), sulphur ($^{35}S$), tritium ($^{3}H$), indium ($^{112}In$), and technetium ($^{99m}Tc$), and fluorescent labels, such as fluorescein and rhodamine, and biotin.

In addition to assaying CD33-like protein levels in a biological sample obtained from an individual, CD33-like protein can also be detected in vivo by imaging. Antibody labels or markers for in vivo imaging of CD33-like protein include those detectable by X-radiography, NMR or ESR. For X-radiography, suitable labels include radioisotopes such as barium or caesium, which emit detectable radiation but are not overtly harmful to the subject. Suitable markers for NMR and ESR include those with a detectable characteristic spin, such as deuterium, which may be incorporated into the antibody by labeling of nutrients for the relevant hybridoma.

A CD33-like protein-specific antibody or antibody fragment which has been labeled with an appropriate detectable imaging moiety, such as a radioisotope (for example, $^{131}I$, $^{112}In$, $^{99m}Tc$), a radio-opaque substance, or a material detectable by nuclear magnetic resonance, is introduced (for example, parenterally, subcutaneously or intraperitoneally) into the mammal to be examined for cancer. It will be understood in the art that the size of the subject and the imaging system used will determine the quantity of imaging moiety needed to produce diagnostic images. In the case of a radioisotope moiety, for a human subject, the quantity of radioactivity injected will normally range from about 5 to 20 millicuries of $^{99m}Tc$. The labeled antibody or antibody fragment will then preferentially accumulate at the location of cells which contain CD33-like protein. In vivo tumor imaging is described in S. W. Burchiel et al., "Immunopharmacokinetics of Radiolabelled Antibodies and Their Fragments" (Chapter 13 in *Tumor Imaging: The Radiochemical Detection of Cancer*, eds., S. W. Burchiel and B. A. Rhodes, Masson Publishing Inc. (1982)).

CD33-like-protein specific antibodies for use in the present invention can be raised against the intact CD33-like protein or an antigenic polypeptide fragment thereof, which may presented together with a carrier protein, such as an albumin, to an animal system (such as rabbit or mouse) or, if it is long enough (at least about 25 amino acids), without a-carrier.

As used herein, the term "antibody" (Ab) or "monoclonal antibody" (MoAb) is meant to include intact molecules as well as antibody fragments (such as, for example, Fab and F(ab')$_2$ fragments) which are capable of specifically binding to CD33-like protein. Fab and F(ab')$_2$ fragments lack the Fc fragment of intact antibody, clear more rapidly from the circulation, and may have less non-specific tissue binding of an intact antibody (Wahl et al., *J. Nucl. Med.* 24:316-325 (1983)). Thus, these fragments are preferred.

The antibodies of the present invention may be prepared by any of a variety of methods. For example, cells expressing the CD33-like protein or an antigenic fragment thereof can be administered to an animal in order to induce the production of sera containing polyclonal antibodies. In a preferred method, a preparation of CD33-like protein is prepared and purified to render it substantially free of natural contaminants. Such a preparation is then introduced into an animal in order to produce polyclonal antisera of greater specific activity.

In the most preferred method, the antibodies of the present invention are monoclonal antibodies (or CD33-like protein binding fragments thereof). Such monoclonal antibodies can be prepared using hybridoma technology (Kohler et al., *Nature* 256:495 (1975); Kohler et al., *Eur. J. Immunol.* 6:511 (1976); Kohler et al., *Eur. J. Immunol.* 6:292 (1976); Hammerling et al., In: *Monoclonal Antibodies and T-Cell Hybridomas*, Elsevier, N.Y., pp. 563-681 (1981)). In general, such procedures involve immunizing an animal (preferably a mouse) with a CD33-like protein antigen or, more preferably, with a CD33-like protein-expressing cell. Suitable cells can be recognized by their capacity to bind anti-CD33-like protein antibody. Such cells may be cultured in any suitable tissue culture medium; however, it is preferable to culture cells in Earle's modified Eagle's medium supplemented with 10% fetal bovine serum (inactivated at about 56° C.), and supplemented with about 10 µg/l of nonessential amino acids, about 1,000 U/ml of penicillin, and about 100 µg/ml of streptomycin. The splenocytes of such mice are extracted and fused with a suitable myeloma cell line. Any suitable myeloma cell line may be employed in accordance with the present invention; however, it is preferable to employ the parent myeloma cell line (SP$_2$O), available from the American Type Culture Collection, Manassas, Va. After fusion, the resulting hybridoma cells are selectively maintained in HAT medium, and then cloned by limiting dilution as described by Wands et al. (*Gastroenterology* 80:225-232 (1981)). The hybridoma cells obtained through such a selection are then assayed to identify clones which secrete antibodies capable of binding the CD33-like protein antigen.

Alternatively, additional antibodies capable of binding to the CD33-like protein antigen may be produced in a two-step procedure through the use of anti-idiotypic antibodies. Such a method makes use of the fact that antibodies are themselves antigens, and that, therefore, it is possible to obtain an antibody which binds to a second antibody. In accordance with this method, CD33-like-protein specific antibodies are used to immunize an animal, preferably a mouse. The splenocytes of such an animal are then used to produce hybridoma cells, and the hybridoma cells are screened to identify clones which produce an antibody whose ability to bind to the CD33-like protein-specific antibody can be blocked by the CD33-like protein antigen. Such antibodies comprise anti-idiotypic antibodies to the CD33-like protein-specific antibody and can be used to immunize an animal to induce formation of further CD33-like protein-specific antibodies.

It will be appreciated that Fab and F(ab')$_2$ and other fragments of the antibodies of the present invention may be used according to the methods disclosed herein. Such fragments are typically produced by proteolytic cleavage, using enzymes such as papain (to produce Fab fragments) or pepsin (to produce F(ab')$_2$ fragments). Alternatively, CD33- like protein-binding fragments can be produced through the application of recombinant DNA technology or through synthetic chemistry.

Where in vivo imaging is used to detect enhanced levels of CD33-like protein for tumor diagnosis in humans, it may be preferable to use "humanized" chimeric monoclonal antibodies. Such antibodies can be produced using genetic constructs derived from hybridoma cells producing the monoclonal antibodies described above. Methods for producing chimeric antibodies are known in the art. See, for review, Morrison, *Science* 229:1202 (1985); Oi et al., *BioTechniques* 4:214 (1986); Cabilly et al., U.S. Pat. No. 4,816,567; Taniguchi et al., EP 171496; Morrison et al., EP 173494; Neuberger et al., WO 8601533; Robinson et al., WO 8702671; Boulianne et al., *Nature* 312:643 (1984); Neuberger et al., *Nature* 314:268 (1985).

Further suitable labels for the CD33-like protein-specific antibodies of the present invention are provided below. Examples of suitable enzyme labels include malate dehydrogenase, staphylococcal nuclease, delta-5-steroid isomerase, yeast-alcohol dehydrogenase, alpha-glycerol phosphate dehydrogenase, triose phosphate isomerase, peroxidase, alkaline phosphatase, asparaginase, glucose oxidase, beta-galactosidase, ribonuclease, urease, catalase, glucose-6-phosphate dehydrogenase, glucoamylase, and acetylcholine esterase.

Examples of suitable radioisotopic labels include $^{3}$H, $^{111}$In, $^{125}$I, $^{131}$I, $^{32}$P, $^{35}$S, $^{14}$C, $^{51}$Cr, $^{57}$To, $^{58}$Co, $^{59}$Fe, $^{75}$Se, $^{152}$Eu, $^{90}$Y, $^{67}$Cu, $^{217}$Ci, $^{211}$At, $^{212}$Pb, $^{47}$Sc, $^{109}$Pd, etc. $^{111}$In is a preferred isotope where in vivo imaging is used since its avoids the problem of dehalogenation of the $^{125}$I or $^{131}$I-labeled monoclonal antibody by the liver. In addition, this radionucleotide has a more favorable gamma emission energy for imaging (Perkins et al., *Eur. J. Nucl. Med.* 10:296-301 (1985); Carasquillo et al., *J. Nucl. Med.* 28:281-287 (1987)). For example, $^{111}$In coupled to monoclonal antibodies with 1-(P-isothiocyanatobenzyl)-DPTA has shown little uptake in non-tumorous tissues, particularly the liver, and therefore enhances specificity of tumor localization (Esteban et al., *J. Nucl. Med.* 28:861-870 (1987)).

Examples of suitable non-radioactive isotopic labels include $^{157}$Gd, $^{55}$Mn, $^{162}$Dy, $^{52}$Tr, and $^{56}$Fe.

Examples of suitable fluorescent labels include an $^{152}$Eu label, a fluorescein label, an isothiocyanate label, a rhodamine label, a phycoerythrin label, a phycocyanin label, an allophycocyanin label, an o-phthaldehyde label, and a fluorescamine label.

Examples of suitable toxin labels include diphtheria toxin, ricin, and cholera toxin.

Examples of chemiluminescent labels include a luminal label, an isoluminal label, an aromatic acridinium ester label, an imidazole label, an acridinium salt label, an oxalate ester label, a luciferin label, a luciferase label, and an aequorin label.

Examples of nuclear magnetic resonance contrasting agents include heavy metal nuclei such as Gd, Mn, and iron.

Typical techniques for binding the above-described labels to antibodies are provided by Kennedy et al. (*Clin. Chim. Acta* 70:1-31 (1976)), and Schurs et al. (*Clin. Chim. Acta* 81:1-40 (1977)). Coupling techniques mentioned in the latter are the glutaraldehyde method, the periodate method, the dimaleimide method, the m-maleimido-benzyl-N-hydroxy-succinimide ester method, all of which methods are incorporated by reference herein.

Therapeutics

CD33 is expressed by clonogenic leukemic cells from about 90% of patients with acute myeloid leukemia (AML). While about 60-70% of adults suffering from AML experience complete remission after chemotherapy, most of these patients will ultimately die of relapsed leukemia (Robertson et al., *Blood* 79:2229-2236 (1992)). It is believed that, like CD33, the CD33-like protein of the present invention is also expressed by clonogenic leukemic cells from the vast majority of patients with AML.

Postremission therapy is more successful when patients are treated with an allogeneic bone marrow transplant. However, this mode of therapy is often unavailable to an individual because of their age or because of the lack of an appropriate donor. An alternative treatment utilizes autologous bone marrow harvested while the patient was in remission. However, if residual leukemia cells exist, such an allograft could result in relapse for the patient. Consequently, a need exists for methods of purging leukemic cells from the autografts of patients with advanced AML. Such a method would ideally involve the use of a cytotoxic agent capable of selectively eliminating or removing tumor cells while sparing the hematopoietic stem cells necessary for engraftment. Studies have shown that the majority of leukemia cells are incapable of sustained replication; these cells are, however, produced by a small number of leukemic "stem cells" which appear to have a different surface antigen phenotype from the other cells, i.e., they are believed to lack the CD33-like protein antigen of the present invention.

By the invention, a method is provided for purging leukemic hematopoietic cells from the autografts of patients with AML. The method involves obtaining bone marrow (BM) from an AML patient by, for example, percutaneous aspirations from the posterior iliac crest, isolating BM mononuclear by Ficoll-hypaque density gradient centrifugation, and incubating with an anti-CD33-like protein monoclonal antibody (MoAb), for example, 3-5 times for 15-30 minutes at 4-6° C., followed by incubation with rabbit complement at about 37° C. for 30 minutes. (Rabbit complement tested for optimal specific cytotoxicity can be obtained as described in Roy et al., *Leuk Res* 14:407 (1990)). The patient is then subject to myeloablative chemotherapy as described in Robertson et al., *Blood* 79 (9):2229 (1992), followed by reinfusion of the treated autologous BM according to standard technique. By the invention, clonogenic tumor cells are depleted from the marrow while sparing hematopoietic cells necessary for engraftment.

In a further embodiment, the invention provides an in vivo method for selectively killing or inhibiting growth of tumor cells expressing the CD33-like protein antigen of the present invention. Such tumor cells include metastatic tumors, leukemias and lymphomas. The method involves administering to a patient an effective amount of an antagonist to inhibit the CD33-like protein receptor signaling pathway. By the invention, administering such antagonist of the CD33-like protein to a patient is also useful for treating inflammatory diseases including arthritis and colitis.

Antagonists for use in the present invention include polyclonal and monoclonal antibodies raised against the CD33-like polypeptides or a fragment thereof. Such antagonist antibodies raised against CD33-like polypeptides can be generated as described in Caron et al., *Cancer Research* 52:6761 (1992); Juric et al., *Cancer Research* (*Suppl.*) 55:5908s-5910s (1995); and Robertson et al., *Blood* 79:2229-2236 (1992).

Other potential antagonists include antisense molecules. Antisense technology can be used to control gene expression through antisense DNA or RNA or through triple-helix formation. Antisense techniques are discussed, for example, in Okano, J., *Neurochem.* 56:560 (1991); *Oligodeoxynucleotides as Antisense Inhibitors of Gene Expression*, CRC Press, Boca Raton, Fla. (1988). Triple helix formation is discussed in, for instance Lee et al., *Nucleic Acids Research* 6:3073 (1979); Cooney et al., *Science* 241:456 (1988); and Dervan et al., *Science* 251:1360 (1991). The methods are based on binding of a polynucleotide to a complementary DNA or RNA. For example, the 5' coding portion of a polynucleotide that encodes the mature polypeptide of the present invention may be used to design an antisense RNA oligonucleotide of from about 10 to 40 base pairs in length. A DNA oligonucleotide is designed to be complementary to a region of the gene involved in transcription thereby preventing transcription and the production of the receptor. The antisense RNA oligonucleotide hybridizes to the mRNA in vivo and blocks translation of the mRNA molecule into receptor polypeptide. The oligonucleotides described above can also be delivered to cells such that the antisense RNA or DNA may be expressed in vivo to inhibit production of the receptor.

Further antagonist according to the present invention include soluble forms of CD33-like protein, i.e., CD33-like protein fragments that include the extracellular region from the full length receptor. Such soluble forms of the receptor, which may be naturally occurring or synthetic, antagonize CD33-like protein mediated signaling by competing with the cell surface CD33-like protein for binding to CD33 receptor ligands.

As indicated polyclonal and monoclonal antibody antagonists according to the present invention can be raised according to the methods disclosed in WO 93/20848 and U.S. Pat. No. 5,239,062. The term "antibody" (Ab) or "monoclonal antibody" (MoAb) as used herein is meant to include intact molecules as well as fragments thereof (such as, for example, Fab and F(ab')$_2$ fragments) which are capable of binding an antigen. Fab and F(ab')$_2$ fragments lack the Fc fragment of intact antibody, clear more rapidly from the circulation, and may have less non-specific tissue binding of an intact antibody (Wahl et al., *J. Nucl. Med.* 24:316-325 (1983)).

Antibodies according to the present invention may be prepared by any of a variety of methods using CD33-like protein immunogens of the present invention. As indicated, such CD33-like protein immunogens include the full length CD33-like protein polypeptide (which may or may not include the leader sequence) and CD33-like protein polypeptide fragments such as the extracellular domain, the transmembrane domain, and the intracellular domain.

In a preferred method, antibodies according to the present invention are MoAbs. Such MoAbs can be prepared using hybridoma technology as described above (Kohler and Millstein, *Nature* 256:495-497 (1975) and U.S. Pat. No. 4,376,110; Harlow et al., *Antibodies: A Laboratory Manual*, Cold Spring Harbor Laboratory Press, Cold Spring Harbor, N.Y., 1988; *Monoclonal Antibodies and Hybridomas: A New Dimension in Biological Analyses*, Plenum Press, New York, N.Y., 1980; Campbell, "Monoclonal Antibody Technology," In: *Laboratory Techniques in Biochemistry and Molecular Biology*, Volume 13 (Burdon et al., eds.), Elsevier, Amsterdam (1984)).

Also intended within the scope of the present invention are humanized chimeric antibodies, produced using genetic constructs derived from hybridoma cells producing the MoAbs described above. Methods for production of chimeric antibodies are known in the art. See, for review: Morrison, *Science*, 229:1202-1207 (1985); Oi et al., *BioTechniques* 4:214 (1986); see, also: Cabilly et al., U.S. Pat. No. 4,816,567 (Mar. 28, 1989); Taniguchi et al., EPO Patent Public. EP171496 (Feb. 19, 1986); Morrison et al., EPO Patent Pub. EP173494 (Mar. 5, 1986); Neuberger et al., PCT Pub. WO8601533 (Mar. 13, 1986); Robinson et al., PCT Pub. WO 8702671 (May 7, 1987); Boulianne et al., *Nature* 312:643-646 (1984); Neuberger et al., *Nature* 314:268-270 (1985).

A particularly preferred method for generating an anti-CD33-like protein humanized MoAb is described in Caron et al., *Cancer Res* 52:6761(1992).

Proteins and other compounds which bind the CD33-like protein domains are also candidate antagonist according to the present invention. Such binding compounds can be "captured" using the yeast two-hybrid system (Fields and Song, *Nature* 340:245-246 (1989)). A modified version of the yeast two-hybrid system has been described by Roger Brent and his colleagues (Gyuris, J. et al., *Cell* 75:791-803 (1993); Zervos, A. S. et al., *Cell* 72:223-232 (1993)). Briefly, a domain of the CD33-like polypeptide is used as bait for binding compounds. Positives are then selected by their ability to grow on plates lacking leucine, and then further tested for their ability to turn blue on plates with X-gal, as previously described in great detail (Gyuris, J. et al., *Cell* 75:791-803 (1993)). Preferably, the yeast two-hybrid system is used according to the present invention to capture compounds which bind to either the CD33-like extracellular ligand binding domain or to the CD33-like protein intracellular domain. Such compounds are good candidate antagonists of the present invention. This system has been used previously to isolate proteins which bind to the intracellular domain of the p55 and p75 TNF receptors (WO 95/31544).

The invention further provides methods for using the CD33-like protein binding compounds described above as vehicles for selective killing of tumor cells.

The specificity of the binding compounds to the CD33-like protein can be determined by their affinity. Such specificity exists if the dissociation constant ($K_D$=1/K, where K is the affinity constant) of the moiety is <1 μM, preferably <100 nM, and most preferably <1 nM. Antibody molecules will typically have a $K_D$ in the lower ranges. $K_D$=[R-L]/[R][L] where [R], [L], and [R-L] are the concentrations at equilibrium of the receptor or CD33-like protein (R), ligand, antibody, or peptide (L) and receptor-ligand complex (R-L), respectively. Typically, the binding interactions between ligand or peptide and receptor or antigen include reversible noncovalent associations such as electrostatic attraction, Van der Waals forces, and hydrogen bonds.

Other assay formats may involve the detection of the presence or absence of various physiological or chemical changes that result from the interaction, such as down modulation, internalization, or an increase in phosphorylation, as described in Receptor-Effector Coupling-A Practical Approach, ed. Hulme, IRL Press, Oxford (1990).

Gelonin is a glycoprotein (m.w. approximately 29-30,000 Kd) purified from the seeds of Gelonium multiforum. Gelonin belongs to a class of potent ribosomal-inactivating plant toxins. Other members of this class of ribosomal inactivating plant toxins are the chains of abrin, ricin and modeccin. Gelonin, like abrin and ricin, inhibits protein synthesis by damaging the 60S sub-unit of mammalian ribosomes. Gelonin appears to be stable to chemical and physical treatment. Furthermore, gelonin itself does not bind to cells and, therefore, is non-toxic (except in high concentrations) and is safe to manipulate in the laboratory., The inactivation of ribosomes is irreversible, does not appear to involve cofactors and occurs with an efficiency which suggests that gelonin acts enzymatically.

Gelonin and ricin are among the most active toxins which inhibit protein synthesis on a protein weight basis. Gelonin is 10 to 1000 times more active in inhibiting protein synthesis than ricin A chain. Peptides like ricin and abrin are composed of two chains, an A chain which is the toxic unit and a B chain which acts by binding to cells. Unlike ricin and abrin, gelonin is composed of a single chain, and because it lacks a B chain for binding to cells, it is itself relatively non-toxic to intact cells.

Mammalian cells apparently lack the ability to bind and/or to internalize the native gelonin molecule. Conjugates of gelonin with a CD33-like protein binding compound of the present invention provide both a specific method for binding the gelonin to the cell and a route for internalization of the gelonin-binding compound complex.

Where the CD33-like protein binding compound is a MoAb, the cytotoxic moiety of the immunotoxin may be a cytotoxic drug or an enzymatically active toxin of bacterial or plant origin, or an enzymatically active fragment ("A chain") of such a toxin. Enzymatically active toxins and fragments thereof are preferred and are exemplified by gelonin, diphtheria A chain, nonbinding active fragments of diphtheria toxin, exotoxin A chain (from *Pseudomonas aeruginosa*), ricin A chain, abrin A chain, modeccin A chain, alpha sarcin, *Aleurites fordii* proteins, dianthin proteins, *Phytoiacca americana* proteins (PAPI, PAPII, and PAP-S), momordica charantia inhibitor, curcin, crotin, saponaria officinalis inhibitor, mitogellin, restrictocin, phenomycin, and enomycin. Most preferred is the conjugation with gelonin.

Biological response modifiers which may be coupled to the anti-CD33-like protein MoAb to form an immunotoxin include, but are not limited to, lymphokines and cytokines such as IL-1, IL-2, interferons (alpha, beta or gamma), TNF, LT, TGF-beta and IL-6. These biological response modifiers have a variety of effects on tumor cells. Among these are increased tumor cell killing by direct action as well as increased tumor cell killing by increased host defense mediated processes. Conjugation of an MoAb to these biological response modifiers will allow selective localization within tumors and, hence, improved anti-proliferative effects while suppressing non-specific effects leading to toxicity of non-target cells.

Cytotoxic drugs (and derivatives thereof) which are useful in the present invention include, but are not limited to, adriamycin, cis-platinum complex, bleomycin and methotrexate. These cytotoxic drugs are useful for clinical management of recurrent tumors, but their use is complicated by severe side effects and damage caused to non-target cells. The MoAb serves as a useful carrier of such drugs providing an efficient means of both delivery to the tumor and enhanced entry into the tumor cells themselves. In addition, specified antibody delivery of cytotoxic drugs to tumors will provide protection of sensitive sites such as the liver that do not express CD33-like protein and bone marrow stem cells from the deleterious action of the chemotherapeutic agents. Use of drugs conjugated to the carrier antibody as a delivery system allows lower dosage of the drug itself, since all drug moieties are conjugated to antibodies which concentrate within the tumor or leukemia.

Conjugates of the monoclonal antibody may be made using a variety of bifunctional protein coupling agents. Examples of such reagents are SPDP, iminothiolante (IT), bifunctional derivatives of imidoesters such as dimethyl adipimidate, HCl, active esters such as disuccinimidyl suberate, aldehydes such as glutaraldehyde, bis-azido compounds such as bib(p-azidobenzoyl) hexanediamine, bis-diazonium derivatives such as bi-(p-diazoniumbenzoyl) ethylenediamine, diisocyanates such as tolyene 2,6-diisocyanate, and bis-active fluorine compounds such as a 1,5-difluoro-2,4-dinitrobenzene.

When used in vivo for therapy, the immunotoxins are administered to the human or animal patient in therapeutically effective amounts, i.e., amounts that eliminate or reduce the tumor burden or in amounts to eliminate residual disease after an earlier treatment with chemotherapy or radiation therapy. They will normally be administered parenterally, preferably intravenously. The dose and dosage regimen will depend upon the nature of the leukemia and its population, the characteristics of the particular immunotoxin, e.g., its therapeutic index, the patient, and the patient's history. The amount of immunotoxin administered will typically be in the range of about 0.01 to about 1.0 mg/kg of patient weight.

For parenteral administration the immunotoxins will be formulated in a unit dosage injectable form (solution, suspension, emulsion) in association with a pharmaceutically acceptable parenteral vehicle. Such vehicles are inherently non-toxic and non-therapeutic. Examples of such vehicles are water, saline, Ringer's solution, dextrose solution, and 5% human serum albumin. Nonaqueous vehicles such as fixed oils and ethyl oleate may also be used. Liposomes may be used as carriers. The vehicle may contain minor amounts of additives such as substances that enhance isotoxicity and chemical stability, e.g., buffers and preservatives. The immunotoxin will typically be formulated in such vehicles at concentrations of about 0.1 mg/ml to 10 mg/ml.

The immunotoxins of the present invention may also be used in a method of killing tumor cells in bone marrow. In this method, the bone marrow is first removed from an individual having a neoplastic disease such as leukemia. Subsequently, the bone marrow is treated with a cytocidally effective dose of an immunotoxin of the present invention.

Having generally described the invention, the same will be more readily understood by reference to the following examples, which are provided by way of illustration and are not intended as limiting.

EXAMPLES

Example 1

Expression in *E. coli*

The DNA sequence encoding the CD33-like protein in the deposited polynucleotide is amplified using PCR oligonucleotide primers specific to the amino acid carboxyl terminal sequence of the CD33-like protein and to vector sequences 3' to the gene. Additional nucleotides containing restriction sites to facilitate cloning are added to the 5' and 3' sequences respectively.

The 5' oligonucleotide primer has the sequence: 5'CGC CCATGGAGAAGCCAGTGTACGAG 3' (SEQ ID NO:4) containing the underlined NcoI restriction site, which encodes a start AUG within the NcoI site, followed by 17 nucleotides of the CD33-like protein cDNA having the nucleotide sequence shown at nucleotide position 85-102 in FIG. 1A-1C (SEQ ID NO:1).

The 3' primer has the sequence: 5' CGC AAGCTTTCAAGAGCCGCTCTGGGACCC 3' (SEQ ID NO:5) containing the underlined HindI restriction site and 18 nucleotides of the CD33-like protein cDNA having a nucleotide sequence complementary to the nucleotide sequence shown at nucleotide position 1285-1302 in FIG. 1A-1C (SEQ ID NO:1).

The restrictions sites are convenient to restriction enzyme sites in the bacterial expression vector pQE-60, which is used for bacterial expression in these examples. (Qiagen, Inc. 9259 Eton Avenue, Chatsworth, Calif., 91311). pQE60 encodes ampicillin antibiotic resistance ("Ampr") and contains a bacterial origin of replication ("ori"), an IPTG inducible promoter, a ribosome binding site ("RBS"), a 6-His tag and restriction enzyme sites.

The amplified DNA and the vector pQE60 both are digested with NcoI and HindIII and then ligated together. Inserting amplified cDNA encoding the CD33-like protein into pQE60 places the coding region downstream of and operably linked to the vector's IPTG-inducible promoter, and in-frame with an initiating AUG appropriately positioned for translation of the CD33-like protein.

The ligation mixture is transformed into competent *E. coli* cells using standard procedures. Such procedures are described in Sambrook et al., *Molecular Cloning: A Laboratory Manual,* 2nd Ed.; Cold Spring Harbor Laboratory Press, Cold Spring Harbor, N.Y. (1989). *E. coli* strain M15/rep4, containing multiple copies of the plasmid pREP4, which expresses lac repressor and confers kanamycin resistance ("Kanr"), is used in carrying out the illustrative example described here. This strain, which is only one of many that are suitable for expressing the CD33-like protein, is available commercially from Qiagen.

Transformants are identified by their ability to grow on LB plates in the presence of ampicillin. Plasmid DNA is isolated from resistant colonies and the identity of the cloned DNA is confirmed by restriction analysis.

Clones containing the desired constructs are grown overnight ("O/N") in liquid culture in LB media supplemented with both ampicillin (100 ug/ml) and kanamycin (25 ug/ml).

The O/N culture is used to inoculate a large culture, at a dilution of approximately 1:100 to 1:250. The cells are grown to an optical density at 600 nm ("OD600") of between 0.4 and 0.6. Isopropyl-B-D-thiogalactopyranoside ("IPTG") is then added to a final concentration of 1 mM to induce transcription from lac repressor sensitive promoters, by inactivating the lacI repressor. Cells subsequently are incubated further for 3 to 4 hours. Cells are then harvested by centrifugation and disrupted, by standard methods. Inclusion bodies are purified from the disrupted cells using routine collection techniques, and protein is solubilized from the inclusion bodies into 8M urea. The 8M urea solution containing the solubilized protein is passed over a PD-10 column in 2× phosphate buffered saline ("PBS"), thereby removing the urea, exchanging the buffer and refolding the protein. Expressed protein is purified by a further step of chromatography to remove endotoxin. Then, it is sterile filtered. The sterile filtered protein preparation is stored in 2× PBS at a concentration of 95 micrograms per ml.

Example 2

Expression in Mammalian Cells (CHO, COS and others).

Most of the vectors used for the transient expression of the cDNA encoding the CD33-like protein in mammalian cells should carry the SV40 origin of replication. This allows the replication of the vector to high copy numbers in cells (e.g. COS cells) which express the T antigen required for the initiation of viral DNA synthesis. Any other mammalian cell line can also be utilized for this purpose.

A typical mammalian expression vector contains the promoter element, which mediates the initiation of transcription of mRNA, the protein coding sequence, and signals required for the termination of transcription and polyadenylation of the transcript. Additional elements include enhancers, Kozak sequences and intervening sequences flanked by donor and acceptor sites for RNA splicing. Highly efficient transcription can be achieved with the early and late promoters from SV40, the long terminal repeats (LTRs) from retroviruses, e.g. RSV, HTLVI, HIVI and the early promoter of the cytomegalovirus (CMV). However, also cellular signals can be used (e.g. human actin, promoter). Suitable expression vectors for use in practicing the present invention include, for example, vectors such as pSVL and pMSG (Pharmacia, Uppsala, Sweden), pRSVcat (ATCC 37152), pSV2dhfr (ATCC 37146) and pBC12MI (ATCC 67109). Mammalian host cells that could be used include, human HeLa, 283, H9 and Jurkart cells, mouse NIH3T3 and C127 cells, Cos 1, Cos 7 and CV1 African green monkey cells, quail QC1-3 cells, mouse L cells and Chinese hamster ovary cells.

Alternatively, the gene can be expressed in stable cell lines that contain the gene integrated into a chromosome. The co-transfection with a selectable marker such as dhfr, gpt, neomycin, hygromycin allows the identification and isolation of the transfected cells.

The transfected gene can also be amplified to express large amounts of the encoded protein. The DHFR (dihydrofolate reductase) is a useful marker to develop cell lines that carry several hundred or even several thousand copies of the gene of interest. Another useful selection marker is the enzyme glutamine synthase (G S) (Murphy et al. *Biochem J.* 227:277-275 (1991), Bebbington et al., *Bio/Technology* 10:163-175 (1992)). Using these markers, the mammalian cells are grown in selective medium and the cells with the highest resistance are selected These cell lines contain the amplified gene(s) integrated into a chromosome. Chinese hamster ovary (CHO) cells are often used for the production of proteins.

The expression vectors pC1 and pC4 contain the strong promoter (LTR) of the Rous Sarcoma Virus (Cullen et al., *Molecular and Cellular Biology,* 438-4470 (March 1985)) plus a fragment of the CMV-enhancer (Boshart et al., *Cell* 41:521-530 (1985). Multiple cloning sites, e.g. with the restriction enzyme cleavage sites BamHI, XbaI and Asp718, facilitate the cloning of the gene of interest. The vectors contain in addition the 3' intron, the polyadenylation and termination signal of the rat preproinsulin gene.

Example 2A

Expression of Extracellular Soluble Domain of CD33-Like Protein in COS Cells

The expression plasmid is made by cloning a cDNA encoding CD33-like protein into the expression vector pcDNAI/Amp (which can be obtained from Invitrogen, Inc.).

The expression vector pcDNAI/amp contains: (1) an *E. coli* origin of replication effective for propagation in *E. coli* and other prokaryotic cell; (2) an ampicillin resistance gene for selection of plasmid-containing prokaryotic cells; (3) an SV40 origin of replication for propagation in eukaryotic cells; (4) a CMV promoter, a polylinker, an SV40 intron, and a polyadenylation signal arranged so that a cDNA conveniently can be placed under expression control of the CMV promoter and operably linked to the SV40 intron and the polyadenylation signal by means of restriction sites in the polylinker.

A DNA fragment encoding the CD33-like protein extracellular soluble domain and a HA tag fused in frame to its 3' end are cloned into the polylinker region of the vector so that recombinant protein expression is directed by the CMV promoter. The HA tag corresponds to an epitope derived from the influenza hemagglutinin protein described by Wilson et al., Cell 37: 767 (1984). The fusion of the HA tag to the target protein allows easy detection of the recombinant protein with an antibody that recognizes the HA epitope.

The plasmid construction strategy is as follows. The CD33-like protein cDNA of the deposit clone is amplified using primers that contain convenient restriction sites, much as described above for the expression of CD33-like protein in E. coli. To facilitate detection, purification and characterization of the expressed CD33-like protein, one of the primers contains a hemagglutinin tag ("HA tag") as described above.

Suitable primers include the following, which are used in this example: the 5' primer CGC GGATCCGCC ATC ATG CTG CCC CTG CTG CTG 3' (SEQ ID NO:6) contains the underlined BamHI site and the first 18 nucleotides in the coding region of the CD33-like protein cDNA having the nucleotide sequence shown at nucleotide position 37-54 in FIG. 1A-1C (SEQ ID NO:1).

The 3' primer, containing the underlined XbaI site, stop codon, hemagglutinin tag and being complementary to the nucleotide sequence of the last 18 bp preceding the transmembrane domain (bps 1285-1302) shown in FIG. 1 (SEQ ID NO:1), has the following sequence: 5'CGC TCTAGATCA AGC GTA GTC TGG GAC GTC GTA TGG GTA AGA GCC GCT CTG GGA CCC 3' (SEQ ID NO:7).

The PCR amplified DNA fragment and the vector, pcDNAI/Amp, are digested with BamHI and XbaI and then ligated. The ligation mixture is transformed into E. coli strain SURE (available from Stratagene Cloning Systems, 11099 North Torrey Pines Road, La Jolla, Calif. 92037), and the transformed culture is plated on ampicillin media plates which then are incubated to allow growth of ampicillin resistant colonies. Plasmid DNA is isolated from resistant colonies and examined by restriction analysis and gel sizing for the presence of the CD33-like protein-encoding fragment.

For expression of recombinant CD33-like protein, COS cells are transfected with an expression vector, as described above, using DEAE-DEXTRAN, as described, for instance, in Sambrook et al., Molecular Cloning: A Laboratory Manual, Cold Spring Laboratory Press, Cold Spring Harbor, N.Y. (1989). Cells are incubated under conditions for expression of CD33-like protein by the vector. Expression of the CD33-like protein/HA fusion protein is detected by radiolabelling and immunoprecipitation, using methods described in, for example Harlow et al., Antibodies: A Laboratory Manual, 2nd Ed.; Cold Spring Harbor Laboratory Press, Cold Spring Harbor, N.Y. (1988). To this end, two days after transfection, the cells are labeled by incubation in media containing $^{35}$S-cysteine for 8 hours. The cells and the media are collected, and the cells are washed and the lysed with detergent-containing RIPA buffer: 150 mM NaCl, 1% NP-40, 0.1% SDS, 1% NP-40, 0.5% DOC, 50 mM TRIS, pH 7.5, as described by Wilson et al. cited above. Proteins are precipitated from the cell lysate and from the culture media using an HA-specific monoclonal antibody. The precipitated proteins then are analyzed by SDS-PAGE gels and autoradiography. An expression product of the expected size is seen in the cell lysate, which is not seen in negative controls.

Example 2B

Expression and Purification of Human CD33-Like Protein Using the CHO Expression System The DNA sequence encoding CD33-like protein in the deposited polynucleotide is amplified using PCR oligonucleotide primers specific to the carboxyl terminal sequence of the CD33-like protein and to vector sequences 3' to the gene. Additional nucleotides containing restriction sites to facilitate cloning are added to the 5' and 3' sequences respectively.

For both the full length gene and the nucleotide sequence encoding the extracellular soluble domain, the 5' primer has the sequence: 5'CGC GGATCCGCC ATC ATG CTG CCC CTG CTG CTG 3' (SEQ ID NO:9) containing the underlined BamHI restriction site and the first 18 nucleotides in the coding region of the CD33-like protein cDNA having the nucleotide sequence shown at nucleotide position 37-54 in FIG. 1A-1C (SEQ ID NO:1). For the full length gene, the 3' primer has the sequence: 5'CGC GGTACCTCA GTG GCT CCT CCA GCC AGG 3'(SEQ ID NO:8), containing the underlined Asp718 restriction site and nucleotides of the CD33-like protein cDNA having a sequence complementary to the nucleotide sequence shown at nucleotide position 1713-1730 in FIG. 1A-1C (SEQ ID NO:1). For the extracellular domain, the 3' primer has the sequence: 5'CGC GGTACCTCA AGA GCC GCT CTG GGA CCC 3' (SEQ ID NO:10), containing the underlined Asp718 restriction site and 18 nucleotides of the CD33-like protein cDNA having a nucleotide sequence complementary to the nucleotide sequence shown at nucleotide position 1285-1302 in FIG. 1A-1C (SEQ ID NO:1). The restrictions sites are convenient to restriction enzyme sites in the CHO expression vectors PC4.

The amplified CD33-like protein DNA and the vector PC4 both are digested with BamHI and the digested DNAs then ligated together. Insertion of the CD33-like protein DNA into the BamHI restricted vector placed the CD33-like protein coding region downstream of and operably linked to the vector's promoter. The ligation mixture is transformed into competent E. coli cells using standard procedures. Such procedures are described in Sambrook et al., Molecular Cloning: A Laboratory Manual, 2nd Ed.; Cold Spring Harbor Laboratory Press, Cold Spring Harbor, N.Y. (1989).

Example 3

Cloning and Expression of the CD33-Like Protein in a Baculovirus Expression System The cDNA sequences encoding either the soluble extracellular domain or the full length CD33-like protein receptor in the deposited clone is amplified using PCR oligonucleotide primers corresponding to the 5' and 3' sequences of the gene:

The 5' primer for expression of either the extracellular domain or the full length protein has the sequence: 5'CGC GGATCCGCC ATC ATG CTG CCC CTG CTG CTG,3' (SEQ ID NO:9) containing the underlined Bam-HI restriction site and the first 18 nucleotides in the coding region of the CD33-like protein cDNA having the nucleotide sequence shown at nucleotide position 37-54 in FIG. 1A-1C (SEQ ID NO:1). Inserted into an expression vector, as described below, the 5' end of the amplified fragment encoding CD33-like protein provides an efficient signal peptide. An efficient signal for initiation of translation in eukaryotic cells, as described by Kozak, M., *J. Mol. Biol.* 196:947-950 (1987) is appropriately located in the vector portion of the construct.

For the full length gene the 3' primer has the full length sequence: 5'CGC GGTACCTCA GTG GCT CCT CCA GCC AGG 3' (SEQ ID NO:8), containing the underlined Asp718 restriction site and nucleotides of the CD33-like protein cDNA having a sequence complementary to the nucleotide sequence shown at nucleotide position 1713-1730 in FIG. 1A-1C (SEQ ID NO:1). For the extracelluar domain, the 3' primer has the sequence: 5'CGC GGTACCTCAAGA GCC GCT CTG GGA CCC 3' (SEQ ID NO:10), containing the underlined Asp718 restriction site and 18 nucleotides of the CD33-like protein cDNA having a nucleotide sequence complementary to the nucleotide sequence shown at nucleotide position 1285-1302 in FIG. 1A-1C (SEQ ID NO:1).

The amplified fragment is isolated from a 1% agarose gel using a commercially available kit ("Geneclean®," BIO 101 Inc., La Jolla, Calif.). The fragment then is digested with BamHI and Asp718 and again is purified on a 1% agarose gel. This fragment is designated herein F2.

The vector pA2 is used to express the CD33-like protein in the baculovirus expression system, using standard methods, such as those described in Summers et al, *A Manual of Methods for Baculovirus Vectors and Insect Cell Culture Procedures,* Texas Agricultural Experimental Station Bulletin No. 1555 (1987). This expression vector contains the strong polyhedrin promoter of the Autographa californica nuclear polyhedrosis virus (AcMNPV) followed by convenient restriction sites. For an easy selection of recombinant virus the beta-galactosidase gene from *E. coli* is inserted in the same orientation as the polyhedrin promoter and is followed by the polyadenylation signal of the polyhedrin gene. The polyhedrin sequences are flanked at both sides by viral sequences for cell-mediated homologous recombination with wild-type viral DNA to generate viable virus that express the cloned polynucleotide.

Many other baculovirus vectors could be used in place of pA2, such as pAc373, pVL941 and pAcIM1 provided, as those of skill readily will appreciate, that construction provides appropriately located signals for transcription, translation, trafficking and the like, such as an in-frame AUG and a signal peptide, as required. Such vectors are described in Luckow et al., *Virology* 170:31-39, among others.

The plasmid is digested with the restriction enzymes BamHI and Asp718 and then is dephosphorylated using calf intestinal phosphatase, using routine procedures known in the art. The DNA is then isolated from a 1% agarose gel using a commercially available kit ("Geneclean®" BIO 101 Inc., La Jolla, Calif.). This vector DNA is designated herein "V2".

Fragment F2 and the dephosphorylated plasmid V2 are ligated together with T4 DNA ligase. *E. coli* HB101 cells are transformed with ligation mix and spread on culture plates. Bacteria are identified that contain the plasmid with the human CD33-like protein gene by digesting DNA from individual colonies using BamHI and Asp718 and then analyzing the digestion product by gel electrophoresis. The sequence of the cloned fragment is confirmed by DNA sequencing. This plasmid is designated herein pBac/CD33-like protein.

Five µg of the plasmid pBac/CD33-like protein is co-transfected with 1.0 µg of a commercially available linearized baculovirus DNA ("BaculoGold® baculovirus DNA", Pharmingen, San Diego, Calif.), using the lipofection method described by Felgner et al., *Proc. Natl. Acad. Sci. USA* 84:7413-7417 (1987). 1 µg of BaculoGold® virus DNA and 5 µg of the plasmid pBac/CD33-like protein are mixed in a sterile well of a microtiter plate containing 50 µl of serum-free Grace's medium (Life Technologies Inc., Gaithersburg, Md.). Afterwards 10 µl Lipofectin plus 90 µl Grace's medium are added, mixed and incubated for 15 minutes at room temperature. Then the transfection mixture is added drop-wise to Sf9 insect cells (ATCC CRL 1711) seeded in a 35 mm tissue culture plate with 1 ml Grace's medium without serum. The plate is rocked back and forth to mix the newly added solution. The plate is then incubated for 5 hours at 27° C. After 5 hours the transfection solution is removed from the plate and 1 ml of Grace's insect medium supplemented with 10% fetal calf serum is added. The plate is put back into an incubator and cultivation is continued at 27° C. for four days.

After four days the supernatant is collected and a plaque assay is performed, as described by Summers and Smith, cited above. An agarose gel with "Blue Gal" (Life Technologies Inc., Gaithersburg, Md.) is used to allow easy identification and isolation of gal-expressing clones, which produce blue-stained plaques. (A detailed description of a "plaque assay" of this type can also be found in the user's guide for insect cell culture and baculovirology distributed by Life Technologies Inc., Gaithersburg, Md., page 9-10).

Four days after serial dilution, the virus is added to the cells. After appropriate incubation, blue stained plaques are picked with the tip of an Eppendorf pipette. The agar containing the recombinant viruses is then resuspended in an Eppendorf tube containing 200 µl of Grace's medium. The agar is removed by a brief centrifugation and the supernatant containing the recombinant baculovirus is used to infect Sf9 cells seeded in 35 mm dishes. Four days later the supernatants of these culture dishes are harvested and then they are stored at 4° C. A clone containing properly inserted CD33-like protein receptor is identified by DNA analysis including restriction mapping and sequencing. This is designated herein as V-CD33-like protein.

Sf9 cells are grown in Grace's medium supplemented with 10% heat-inactivated FBS. The cells are infected with the recombinant baculovirus V-CD33-like protein at a multiplicity of infection ("MOI") of about 2 (about 1 to about 3). Six hours later the medium is removed and is replaced with SF900 II medium minus methionine and cysteine (available from Life Technologies Inc., Gaithersburg, Md.). Forty-two hours later, 5 µCi of 35S-methionine and 5 µCi 35S cysteine (available from Amersham) are added. The cells are further incubated for 16 hours and then they are harvested by centrifugation, lysed and the labeled proteins are visualized by SDS-PAGE and autoradiography.

Example 4

Tissue Distribution of CD33-Like Protein mRNA Expression

Northern blot analysis was carried out to examine the levels of expression of the gene encoding the CD33-like protein in human tissues, using methods described by, among others, Sambrook et al., cited above. A cDNA probe containing the entire nucleotide sequence of the CD33-like protein of the present invention (SEQ ID NO:1) was labeled with $^{32}P$ using the rediprime DNA labeling system (Amersham Life Science), according to manufacturer's instructions. After labeling, the probe was purified using a CHROMA SPIN-100 column (Clontech Laboratories, Inc.), according to manufacturer's protocol number PT1200-1. The purified labeled probe was then used to examine various human tissues for the expression of the gene encoding the CD33-like protein.

Multiple Tissue Northern (MTN) blots containing various human tissues (H) or human immune system tissues (IM) were obtained from Clontech and were examined with labeled probe using ExpressHyb Hybridization Solution (Clontech) according to manufacturer's protocol number PT1190-1. Following hybridization and washing, the blots were mounted and exposed to film at −70° C. overnight, and films developed according to standard procedures.

As shown in FIG. 3, expression of the gene encoding the CD33-like protein of the present invention was highest in hemopoietic tissues including bone marrow, peripheral blood leucocytes and spleen (FIG. 3, lanes 10, 11, 15, respectively), but can also be detected in other tissue such as the lymph node, appendix, lung and placenta (FIG. 3, lanes 14, 12, 5 and 6, respectively).

It will be clear that the invention may be practiced otherwise than as particularly described in the foregoing description and examples.

Numerous modifications and variations of the present invention are possible in light of the above teachings and, therefore, are within the scope of the appended claims.

The disclosures of all patents, patent applications, and publications referred to herein are hereby incorporated by reference.

What is claimed is:

1. An isolated protein comprising a polypeptide selected from the group consisting of:
    (a) amino acids −15 to 536 in SEQ ID NO:2;
    (b) amino acids −14 to 536 in SEQ ID NO:2;
    (c) amino acids 1 to 536 in SEQ ID NO:2;
    (d) amino acids 1 to 407 in SEQ ID NO:2;
    (e) the complete CD33-like polypeptide encoded by the cDNA clone contained in ATCC Deposit No. 97521;
    (f) the mature CD33-like polypeptide encoded by the cDNA clone contained in ATCC Deposit No. 97521; and
    (g) the CD33-like polypeptide extracellular domain encoded by the cDNA clone contained in ATCC Deposit No. 97521;

wherein said polypeptide mediates sialic acid-dependent red blood cell binding.

2. The isolated protein of claim 1 which comprises polypeptide (a).

3. The isolated protein of claim 1 which comprises polypeptide (b).

4. The isolated protein of claim 1 which comprises polypeptide (c).

5. The isolated protein of claim 1 which comprises polypeptide (d).

6. The isolated protein of claim 1 which comprises polypeptide (e).

7. The isolated protein of claim 1 which comprises polypeptide (f).

8. The isolated protein of claim 1 which comprises polypeptide (g).

9. The protein of claim 1, wherein said protein comprises the Fc portion an immunoglobulin.

10. The protein of claim 1, wherein said protein is glycosylated.

11. The protein of claim 1, wherein said protein is fused to polyethylene glycol.

* * * * *

SEQUENCE LISTING

```
<160> NUMBER OF SEQ ID NOS: 12

<210> SEQ ID NO 1
<211> LENGTH: 2027
<212> TYPE: DNA
<213> ORGANISM: Homo sapiens
<220> FEATURE:
<221> NAME/KEY: CDS
<222> LOCATION: (37)..(1689)
<223> OTHER INFORMATION:
<220> FEATURE:
<221> NAME/KEY: sig_peptide
<222> LOCATION: (37)..(81)
<223> OTHER INFORMATION:
<220> FEATURE:
<221> NAME/KEY: mat_peptide
<222> LOCATION: (82)..()
<223> OTHER INFORMATION:

<400> SEQUENCE: 1
ggcacgagct gggctggggc cctggcggat ggagac atg ctg ccc ctg ctg ctg        54
                                        Met Leu Pro Leu Leu Leu
                                        -15             -10 ctg ccc ctg ctg tgg ggg ggg tcc ctg cag gag aag cca gtg tac gag      102
Leu Pro Leu Leu Trp Gly Gly Ser Leu Gln Glu Lys Pro Val Tyr Glu
            -5              -1  1                   5 ctg caa gtg cag aag tcg gtg acg gtg cag gag ggc ctg tgc gtc ctt      150
Leu Gln Val Gln Lys Ser Val Thr Val Gln Glu Gly Leu Cys Val Leu
        10                  15                  20 gtg ccc tgc tcc ttc tct tac ccc tgg aga tcc tgg tat tcc tct ccc      198
Val Pro Cys Ser Phe Ser Tyr Pro Trp Arg Ser Trp Tyr Ser Ser Pro
    25                  30                  35 cca ctc tac gtc tac tgg ttc cgg gac ggg gag atc cca tac tac gct      246
Pro Leu Tyr Val Tyr Trp Phe Arg Asp Gly Glu Ile Pro Tyr Tyr Ala
40                  45                  50                  55 gag gtt gtg gcc aca aac aac cca gac aga aga gtg aag cca gag acc      294
Glu Val Val Ala Thr Asn Asn Pro Asp Arg Arg Val Lys Pro Glu Thr
                60                  65                  70 cag ggc cga ttc cgc ctc ctt ggg gat gtc cag aag aag aac tgc tcc      342
Gln Gly Arg Phe Arg Leu Leu Gly Asp Val Gln Lys Lys Asn Cys Ser
            75                  80                  85 ctg agc atc gga gat gcc aga atg gag gac acg gga agc tat ttc ttc      390
Leu Ser Ile Gly Asp Ala Arg Met Glu Asp Thr Gly Ser Tyr Phe Phe
        90                  95                  100 cgc gtg gag aga gga agg gat gta aaa tat agc tac caa cag aat aag      438
Arg Val Glu Arg Gly Arg Asp Val Lys Tyr Ser Tyr Gln Gln Asn Lys
    105                 110                 115
```

-continued

| | |
|---|---|
| ctg aac ttg gag gtg aca gcc ctg ata gag aaa ccc gac atc cac ttt<br>Leu Asn Leu Glu Val Thr Ala Leu Ile Glu Lys Pro Asp Ile His Phe<br>120               125               130               135 | 486 |
| ctg gag cct ctg gag tcc ggc cgc ccc aca agg ctg agc tgc agc ctt<br>Leu Glu Pro Leu Glu Ser Gly Arg Pro Thr Arg Leu Ser Cys Ser Leu<br>              140               145               150 | 534 |
| cca gga tcc tgt gaa gcg gga cca cct ctc aca ttc tcc tgg acg ggg<br>Pro Gly Ser Cys Glu Ala Gly Pro Pro Leu Thr Phe Ser Trp Thr Gly<br>155               160               165 | 582 |
| aat gcc ctc agc ccc ctg gac ccc gag acc acc cgc tcc tca gag ctc<br>Asn Ala Leu Ser Pro Leu Asp Pro Glu Thr Thr Arg Ser Ser Glu Leu<br>        170               175               180 | 630 |
| acc ctc acc ccc agg ccc gag gac cat ggc acc aac ctc acc tgt cag<br>Thr Leu Thr Pro Arg Pro Glu Asp His Gly Thr Asn Leu Thr Cys Gln<br>185               190               195 | 678 |
| atg aaa cgc caa gga gct cag gtg acc acg gag aga act gtc cag ctc<br>Met Lys Arg Gln Gly Ala Gln Val Thr Thr Glu Arg Thr Val Gln Leu<br>200               205               210               215 | 726 |
| aat gtc tcc tat gct cca cag acc atc acc atc ttc agg aac ggc ata<br>Asn Val Ser Tyr Ala Pro Gln Thr Ile Thr Ile Phe Arg Asn Gly Ile<br>              220               225               230 | 774 |
| gcc cta gag atc ctg caa aac acc tca tac ctt ccg gtc ctg gag ggc<br>Ala Leu Glu Ile Leu Gln Asn Thr Ser Tyr Leu Pro Val Leu Glu Gly<br>235               240               245 | 822 |
| cag gct ctg cgg ctg ctc tgt gat gct ccc agc aac ccc cct gca cac<br>Gln Ala Leu Arg Leu Leu Cys Asp Ala Pro Ser Asn Pro Pro Ala His<br>        250               255               260 | 870 |
| ctg agc tgg ttc cag ggc tcc cct gcc ctg aac gcc acc ccc atc tcc<br>Leu Ser Trp Phe Gln Gly Ser Pro Ala Leu Asn Ala Thr Pro Ile Ser<br>265               270               275 | 918 |
| aat acc ggg atc ttg gag ctt cgt cga gta agg tct gca gaa aaa gga<br>Asn Thr Gly Ile Leu Glu Leu Arg Arg Val Arg Ser Ala Glu Lys Gly<br>280               285               290               295 | 966 |
| ggc ttc acc tgc cgc gct cag cac ccg ctg ggc ttc ctg caa att ttt<br>Gly Phe Thr Cys Arg Ala Gln His Pro Leu Gly Phe Leu Gln Ile Phe<br>              300               305               310 | 1014 |
| ctg aat ctc tca gtt tac tcc ctc cca cag ttg ctg ggc ccc tcc tgc<br>Leu Asn Leu Ser Val Tyr Ser Leu Pro Gln Leu Leu Gly Pro Ser Cys<br>              315               320               325 | 1062 |
| tcc tgg gag gct gag ggt ctg cac tgc aga tgc tcc ttt cga gcc tgg<br>Ser Trp Glu Ala Glu Gly Leu His Cys Arg Cys Ser Phe Arg Ala Trp<br>              330               335               340 | 1110 |
| ccg gcc ccc tcc ctg tgc tgg cgg ctt gag gag aag ccg ctg gag ggg<br>Pro Ala Pro Ser Leu Cys Trp Arg Leu Glu Glu Lys Pro Leu Glu Gly<br>345               350               355 | 1158 |
| aac agc agc cag ggc tca ttc aag gtc aac tcc agc tca cct ggt ccc<br>Asn Ser Ser Gln Gly Ser Phe Lys Val Asn Ser Ser Ser Pro Gly Pro<br>360               365               370               375 | 1206 |
| tgg gcc aac agc tcc ctg atc ctc cac ggg ggg ctc aat tcc gac ctc<br>Trp Ala Asn Ser Ser Leu Ile Leu His Gly Gly Leu Asn Ser Asp Leu<br>              380               385               390 | 1254 |
| aaa gtc agc tgc aag gcc tgg aac atc tat ggg tcc cag agc ggc tct<br>Lys Val Ser Cys Lys Ala Trp Asn Ile Tyr Gly Ser Gln Ser Gly Ser<br>395               400               405 | 1302 |
| gtc ctg ctg ctg caa ggg aga tcg aac ctc ggg aca gga gtg gtt cct<br>Val Leu Leu Leu Gln Gly Arg Ser Asn Leu Gly Thr Gly Val Val Pro<br>410               415               420 | 1350 |
| gca gcc ctt ggt ggt gct ggt gtc atg gcc ctg ctc tgt atc tgt ctg<br>Ala Ala Leu Gly Gly Ala Gly Val Met Ala Leu Leu Cys Ile Cys Leu | 1398 |

```
              425                 430                 435
tgc ctc atc ttc ttt tta ata gtg aaa gcc cgc agg aag caa gca gct      1446
Cys Leu Ile Phe Phe Leu Ile Val Lys Ala Arg Arg Lys Gln Ala Ala
440                 445                 450                 455 ggg aga cca gag aaa atg gat gat gaa gac ccc att atg ggt acc atc      1494
Gly Arg Pro Glu Lys Met Asp Asp Glu Asp Pro Ile Met Gly Thr Ile
                460                 465                 470 acc tcg ggt tcc agg aag aag ccc tgg cca gac agc ccc gga gat caa      1542
Thr Ser Gly Ser Arg Lys Lys Pro Trp Pro Asp Ser Pro Gly Asp Gln
                475                 480                 485 gca tct cct cct ggg gat gcc cct ccc ttg gaa gaa caa aag gag ctc      1590
Ala Ser Pro Pro Gly Asp Ala Pro Pro Leu Glu Glu Gln Lys Glu Leu
            490                 495                 500 cat tat gcc tcc ctt agt ttt tct gag atg aag tcg agg gag cct aag      1638
His Tyr Ala Ser Leu Ser Phe Ser Glu Met Lys Ser Arg Glu Pro Lys
            505                 510                 515 gac cag gag gcc cca agc acc acg gag tac tcg gag atc aag aca agc      1686
Asp Gln Glu Ala Pro Ser Thr Thr Glu Tyr Ser Glu Ile Lys Thr Ser
520                 525                 530                 535 aag tgaggatttg cccagagttc agtcctggct ggaggagcca cagcctgtct           1739
Lys gggggaaagg acaagtcagg gaccacttgc tgaagcacga agagcccttg tggcaatgtt    1799
aacattaact gatgtttaag tgctccaagc agagcagaaa gaaaacagat gatggaatta    1859
gagaggtggg ctcaaatcta ggccctggca ctgtcatcaa gcaattcact gcatccctct    1919
gtgcctcagt ttcccattct gtaaatcaga gatcatgcat gctacctcaa aggttgttgt    1979
gaacattaaa gaaatcaaca catggaaatc aaaaaaaaaa aaaaaaaa                 2027

<210> SEQ ID NO 2
<211> LENGTH: 551
<212> TYPE: PRT
<213> ORGANISM: Homo sapiens

<400> SEQUENCE: 2

Met Leu Pro Leu Leu Leu Pro Leu Leu Trp Gly Gly Ser Leu Gln
-15                 -10                 -5                  -1  1

Glu Lys Pro Val Tyr Glu Leu Gln Val Gln Lys Ser Val Thr Val Gln
                5                   10                  15

Glu Gly Leu Cys Val Leu Val Pro Cys Ser Phe Ser Tyr Pro Trp Arg
            20                  25                  30

Ser Trp Tyr Ser Ser Pro Pro Leu Tyr Val Tyr Trp Phe Arg Asp Gly
        35                  40                  45

Glu Ile Pro Tyr Tyr Ala Glu Val Val Ala Thr Asn Asn Pro Asp Arg
50                  55                  60                  65

Arg Val Lys Pro Glu Thr Gln Gly Arg Phe Arg Leu Leu Gly Asp Val
                70                  75                  80

Gln Lys Lys Asn Cys Ser Leu Ser Ile Gly Asp Ala Arg Met Glu Asp
            85                  90                  95

Thr Gly Ser Tyr Phe Phe Arg Val Glu Arg Gly Arg Asp Val Lys Tyr
        100                 105                 110

Ser Tyr Gln Gln Asn Lys Leu Asn Leu Glu Val Thr Ala Leu Ile Glu
    115                 120                 125

Lys Pro Asp Ile His Phe Leu Glu Pro Leu Glu Ser Gly Arg Pro Thr
130                 135                 140                 145

Arg Leu Ser Cys Ser Leu Pro Gly Ser Cys Glu Ala Gly Pro Pro Leu
                150                 155                 160
```

-continued

```
Thr Phe Ser Trp Thr Gly Asn Ala Leu Ser Pro Leu Asp Pro Glu Thr
            165                 170                 175
Thr Arg Ser Ser Glu Leu Thr Leu Thr Pro Arg Pro Glu Asp His Gly
        180                 185                 190
Thr Asn Leu Thr Cys Gln Met Lys Arg Gln Gly Ala Gln Val Thr Thr
    195                 200                 205
Glu Arg Thr Val Gln Leu Asn Val Ser Tyr Ala Pro Gln Thr Ile Thr
210                 215                 220                 225
Ile Phe Arg Asn Gly Ile Ala Leu Glu Ile Leu Gln Asn Thr Ser Tyr
                230                 235                 240
Leu Pro Val Leu Glu Gly Gln Ala Leu Arg Leu Leu Cys Asp Ala Pro
            245                 250                 255
Ser Asn Pro Pro Ala His Leu Ser Trp Phe Gln Gly Ser Pro Ala Leu
        260                 265                 270
Asn Ala Thr Pro Ile Ser Asn Thr Gly Ile Leu Glu Leu Arg Arg Val
    275                 280                 285
Arg Ser Ala Glu Lys Gly Gly Phe Thr Cys Arg Ala Gln His Pro Leu
290                 295                 300                 305
Gly Phe Leu Gln Ile Phe Leu Asn Leu Ser Val Tyr Ser Leu Pro Gln
                310                 315                 320
Leu Leu Gly Pro Ser Cys Ser Trp Glu Ala Glu Gly Leu His Cys Arg
            325                 330                 335
Cys Ser Phe Arg Ala Trp Pro Ala Pro Ser Leu Cys Trp Arg Leu Glu
        340                 345                 350
Glu Lys Pro Leu Glu Gly Asn Ser Ser Gln Gly Ser Phe Lys Val Asn
    355                 360                 365
Ser Ser Ser Pro Gly Pro Trp Ala Asn Ser Ser Leu Ile Leu His Gly
370                 375                 380                 385
Gly Leu Asn Ser Asp Leu Lys Val Ser Cys Lys Ala Trp Asn Ile Tyr
                390                 395                 400
Gly Ser Gln Ser Gly Ser Val Leu Leu Leu Gln Gly Arg Ser Asn Leu
            405                 410                 415
Gly Thr Gly Val Val Pro Ala Ala Leu Gly Gly Ala Gly Val Met Ala
        420                 425                 430
Leu Leu Cys Ile Cys Leu Cys Leu Ile Phe Phe Leu Ile Val Lys Ala
    435                 440                 445
Arg Arg Lys Gln Ala Ala Gly Arg Pro Glu Lys Met Asp Asp Glu Asp
450                 455                 460                 465
Pro Ile Met Gly Thr Ile Thr Ser Gly Ser Arg Lys Lys Pro Trp Pro
                470                 475                 480
Asp Ser Pro Gly Asp Gln Ala Ser Pro Pro Gly Asp Ala Pro Pro Leu
            485                 490                 495
Glu Glu Gln Lys Glu Leu His Tyr Ala Ser Leu Ser Phe Ser Glu Met
        500                 505                 510
Lys Ser Arg Glu Pro Lys Asp Gln Glu Ala Pro Ser Thr Thr Glu Tyr
    515                 520                 525
Ser Glu Ile Lys Thr Ser Lys
530                 535

<210> SEQ ID NO 3
<211> LENGTH: 364
<212> TYPE: PRT
<213> ORGANISM: Homo sapiens
```

-continued

```
<400> SEQUENCE: 3

Met Pro Leu Leu Leu Leu Pro Leu Leu Trp Ala Gly Ala Leu Ala
1               5                   10                  15

Met Asp Pro Asn Phe Trp Leu Gln Val Gln Glu Ser Val Thr Val Gln
            20                  25                  30

Glu Gly Leu Cys Val Leu Val Pro Cys Thr Phe Phe His Pro Ile Pro
        35                  40                  45

Tyr Tyr Asp Lys Asn Ser Pro Val His Gly Tyr Trp Phe Arg Glu Gly
    50                  55                  60

Ala Ile Ile Ser Gly Asp Ser Pro Val Ala Thr Asn Lys Leu Asp Gln
65                  70                  75                  80

Glu Val Gln Glu Thr Gln Gly Arg Phe Arg Leu Leu Gly Asp Pro
                85                  90                  95

Ser Arg Asn Asn Cys Ser Leu Ser Ile Val Asp Ala Arg Arg Arg Asp
            100                 105                 110

Asn Gly Ser Tyr Phe Phe Arg Met Glu Arg Gly Ser Thr Lys Tyr Ser
        115                 120                 125

Tyr Lys Ser Pro Gln Leu Ser Val His Val Thr Asp Leu Thr His Arg
    130                 135                 140

Pro Lys Ile Leu Ile Pro Gly Thr Leu Glu Pro Gly His Ser Lys Asn
145                 150                 155                 160

Leu Thr Cys Ser Val Ser Trp Ala Cys Glu Gln Gly Thr Pro Pro Ile
                165                 170                 175

Phe Ser Trp Leu Ser Ala Ala Pro Thr Ser Leu Gly Pro Arg Thr Thr
            180                 185                 190

His Ser Ser Val Leu Ile Ile Thr Pro Arg Pro Gln Asp His Gly Thr
        195                 200                 205

Asn Leu Thr Cys Gln Val Lys Phe Ala Gly Ala Gly Val Thr Thr Glu
    210                 215                 220

Arg Thr Ile Gln Leu Asn Val Thr Tyr Val Pro Gln Asn Pro Thr Thr
225                 230                 235                 240

Gly Ile Phe Pro Gly Asp Gly Ser Gly Lys Gln Glu Thr Arg Ala Gly
                245                 250                 255

Leu Val His Gly Ala Ile Gly Gly Ala Gly Val Thr Ala Leu Leu Ala
            260                 265                 270

Leu Cys Leu Cys Leu Ile Phe Phe Ile Val Lys Thr His Arg Arg Lys
        275                 280                 285

Ala Ala Arg Thr Ala Val Gly Ser Asn Asp Thr His Pro Thr Thr Gly
    290                 295                 300

Ser Ala Ser Pro Lys His Gln Lys Asn Ser Lys Leu His Gly Pro Thr
305                 310                 315                 320

Glu Thr Ser Ser Cys Ser Gly Ala Ala Pro Thr Val Glu Met Asp Glu
                325                 330                 335

Glu Leu His Tyr Ala Ser Leu Asn Phe His Gly Met Asn Pro Ser Lys
            340                 345                 350

Asp Thr Ser Thr Glu Tyr Ser Glu Val Arg Thr Gln
        355                 360

<210> SEQ ID NO 4
<211> LENGTH: 26
<212> TYPE: DNA
<213> ORGANISM: Homo sapiens

<400> SEQUENCE: 4
```

```
cgcccatgga gaagccagtg tacgag                                              26

<210> SEQ ID NO 5
<211> LENGTH: 30
<212> TYPE: DNA
<213> ORGANISM: Homo sapiens

<400> SEQUENCE: 5
cgcaagcttt caagagccgc tctgggaccc                                          30

<210> SEQ ID NO 6
<211> LENGTH: 33
<212> TYPE: DNA
<213> ORGANISM: Homo sapiens

<400> SEQUENCE: 6
cgcggatccg ccatcatgct gcccctgctg ctg                                      33

<210> SEQ ID NO 7
<211> LENGTH: 57
<212> TYPE: DNA
<213> ORGANISM: Homo sapiens

<400> SEQUENCE: 7
cgctctagat caagcgtagt ctgggacgtc gtatgggtaa gagccgctct gggaccc            57

<210> SEQ ID NO 8
<211> LENGTH: 30
<212> TYPE: DNA
<213> ORGANISM: Homo sapiens

<400> SEQUENCE: 8
cgcggtacct cagtggctcc tccagccagg                                          30

<210> SEQ ID NO 9
<211> LENGTH: 33
<212> TYPE: DNA
<213> ORGANISM: Homo sapiens

<400> SEQUENCE: 9
cgcggatccg ccatcatgct gcccctgctg ctg                                      33

<210> SEQ ID NO 10
<211> LENGTH: 30
<212> TYPE: DNA
<213> ORGANISM: Homo sapiens

<400> SEQUENCE: 10
cgcggtacct caagagccgc tctgggaccc                                          30

<210> SEQ ID NO 11
<211> LENGTH: 459
<212> TYPE: DNA
<213> ORGANISM: Homo sapiens
<220> FEATURE:
<221> NAME/KEY: misc_feature
<222> LOCATION: (10)..(10)
<223> OTHER INFORMATION: May be any nucleotide
<220> FEATURE:
<221> NAME/KEY: misc_feature
<222> LOCATION: (26)..(26)
<223> OTHER INFORMATION: May be any nucleotide
<220> FEATURE:
<221> NAME/KEY: misc_feature
<222> LOCATION: (161)..(161)
```

```
<223> OTHER INFORMATION: May be any nucleotide
<220> FEATURE:
<221> NAME/KEY: misc_feature
<222> LOCATION: (310)..(310)
<223> OTHER INFORMATION: May be any nucleotide
<220> FEATURE:
<221> NAME/KEY: misc_feature
<222> LOCATION: (325)..(325)
<223> OTHER INFORMATION: May be any nucleotide
<220> FEATURE:
<221> NAME/KEY: misc_feature
<222> LOCATION: (328)..(328)
<223> OTHER INFORMATION: May be any nucleotide
<220> FEATURE:
<221> NAME/KEY: misc_feature
<222> LOCATION: (331)..(331)
<223> OTHER INFORMATION: May be any nucleotide
<220> FEATURE:
<221> NAME/KEY: misc_feature
<222> LOCATION: (340)..(341)
<223> OTHER INFORMATION: May be any nucleotide
<220> FEATURE:
<221> NAME/KEY: misc_feature
<222> LOCATION: (349)..(349)
<223> OTHER INFORMATION: May be any nucleotide
<220> FEATURE:
<221> NAME/KEY: misc_feature
<222> LOCATION: (376)..(376)
<223> OTHER INFORMATION: May be any nucleotide
<220> FEATURE:
<221> NAME/KEY: misc_feature
<222> LOCATION: (388)..(388)
<223> OTHER INFORMATION: May be any nucleotide
<220> FEATURE:
<221> NAME/KEY: misc_feature
<222> LOCATION: (392)..(392)
<223> OTHER INFORMATION: May be any nucleotide
<220> FEATURE:
<221> NAME/KEY: misc_feature
<222> LOCATION: (394)..(395)
<223> OTHER INFORMATION: May be any nucleotide
<220> FEATURE:
<221> NAME/KEY: misc_feature
<222> LOCATION: (398)..(398)
<223> OTHER INFORMATION: May be any nucleotide
<220> FEATURE:
<221> NAME/KEY: misc_feature
<222> LOCATION: (402)..(402)
<223> OTHER INFORMATION: May be any nucleotide
<220> FEATURE:
<221> NAME/KEY: misc_feature
<222> LOCATION: (408)..(409)
<223> OTHER INFORMATION: May be any nucleotide
<220> FEATURE:
<221> NAME/KEY: misc_feature
<222> LOCATION: (411)..(412)
<223> OTHER INFORMATION: May be any nucleotide
<220> FEATURE:
<221> NAME/KEY: misc_feature
<222> LOCATION: (415)..(416)
<223> OTHER INFORMATION: May be any nucleotide
<220> FEATURE:
<221> NAME/KEY: misc_feature
<222> LOCATION: (419)..(419)
<223> OTHER INFORMATION: May be any nucleotide
<220> FEATURE:
<221> NAME/KEY: misc_feature
<222> LOCATION: (421)..(421)
<223> OTHER INFORMATION: May be any nucleotide
<220> FEATURE:
<221> NAME/KEY: misc_feature
<222> LOCATION: (428)..(431)
<223> OTHER INFORMATION: May be any nucleotide
<220> FEATURE:
<221> NAME/KEY: misc_feature
<222> LOCATION: (434)..(434)
<223> OTHER INFORMATION: May be any nucleotide
<220> FEATURE:
<221> NAME/KEY: misc_feature
```

<222> LOCATION: (436)..(436)
<223> OTHER INFORMATION: May be any nucleotide
<220> FEATURE:
<221> NAME/KEY: misc_feature
<222> LOCATION: (438)..(439)
<223> OTHER INFORMATION: May be any nucleotide
<220> FEATURE:
<221> NAME/KEY: misc_feature
<222> LOCATION: (442)..(443)
<223> OTHER INFORMATION: May be any nucleotide
<220> FEATURE:
<221> NAME/KEY: misc_feature
<222> LOCATION: (445)..(445)
<223> OTHER INFORMATION: May be any nucleotide
<220> FEATURE:
<221> NAME/KEY: misc_feature
<222> LOCATION: (449)..(450)
<223> OTHER INFORMATION: May be any nucleotide
<220> FEATURE:
<221> NAME/KEY: misc_feature
<222> LOCATION: (459)..(459)
<223> OTHER INFORMATION: May be any nucleotide

<400> SEQUENCE: 11
aattcggcan aggttccggg acgggnagat cccatactac gctgaggttg tggccacaaa      60
caacccagac agaagagtga agccagagac ccagggccga ttccgcctcc ttggggatgt     120
ccagaagaag aactgctccc tgagcatcgg agatccagaa ntggaggaca cgggaagcta     180
tttcttccgc gtggagagag aagggatgt aaaaatatag ctaccaacag aataagctga     240
acttggaggt gacagccctg atagagaaac ccgacatcca cttttttggag cctttggagt     300 tccggtccgn cccaaaaggt tgagntgnag nctttccagn ntcctgttna aggggaccc      360 acttttaaaa ttttcntgga ggggattncc tnanncntg gncccggnna nnacnnttnt     420 ngggttnnn nttnancnna gnncngggnn ctgggaaan                            459

<210> SEQ ID NO 12
<211> LENGTH: 433
<212> TYPE: DNA
<213> ORGANISM: Homo sapiens
<220> FEATURE:
<221> NAME/KEY: misc_feature
<222> LOCATION: (12)..(12)
<223> OTHER INFORMATION: May be any nucleotide
<220> FEATURE:
<221> NAME/KEY: misc_feature
<222> LOCATION: (22)..(22)
<223> OTHER INFORMATION: May be any nucleotide
<220> FEATURE:
<221> NAME/KEY: misc_feature
<222> LOCATION: (412)..(412)
<223> OTHER INFORMATION: May be any nucleotide

<400> SEQUENCE: 12
agcaattcac tncatccctc tntgcctcag tttcccattc tgtaaatcag agatcatgca      60
tgctacctca aaggttgttg tgaacattaa agaaatcaac acatggaaat caaccaacat     120
gggtcctgga acaggcgttg tgctcagtgc tttctggtct ctcttccttg aatagaaagg     180
tcctgctggc aagttctctc aaggctgggg atgaccaggc acaaaaaaca gggcagcaat     240
atgttggtgt cactccccct cccaaaaactc ttcgaagact ccctagggaa agaccagccc     300
ctcagcctgg gcacttggtt catgatgtgg gatcttatat ccttgccaga gtcatatctt     360
ttgcccactt ttacctgcaa tccttgcatt catattcctt gggttccagt cnttcattta     420 tgagaccta ggg                                                        433